US008198513B2

(12) United States Patent
Boets et al.

(10) Patent No.: US 8,198,513 B2
(45) Date of Patent: Jun. 12, 2012

(54) **INSECTICIDAL PROTEINS FROM *BACILLUS THURINGIENSIS***

(75) Inventors: Annemie Boets, Velzeke (BE); Nicole Damme, Kruishoutem (BE); Eva Mathieu, Eke (BE); Stijn Vanneste, Kortrijk (BE); Jeroen Van Rie, Eeklo (BE)

(73) Assignee: Bayer CropScience N.V., Diegem (BE)

( * ) Notice: Subject to any disclaimer, the term of this patent is extended or adjusted under 35 U.S.C. 154(b) by 0 days.

(21) Appl. No.: 13/150,780

(22) Filed: Jun. 1, 2011

(65) Prior Publication Data

US 2011/0277185 A1 Nov. 10, 2011

Related U.S. Application Data

(60) Division of application No. 12/081,208, filed on Apr. 11, 2008, now Pat. No. 7,964,773, which is a division of application No. 11/600,831, filed on Nov. 17, 2006, now Pat. No. 7,361,808, which is a division of application No. 10/614,524, filed on Jul. 8, 2003, now Pat. No. 7,169,971, which is a continuation of application No. 09/739,243, filed on Dec. 19, 2000, now abandoned.

(60) Provisional application No. 60/173,387, filed on Dec. 28, 1999.

(51) Int. Cl.
*C12N 15/82* (2006.01)
*C12N 15/32* (2006.01)
*C12N 1/21* (2006.01)

(52) U.S. Cl. ............... 800/302; 435/252.3; 800/279; 536/23.71

(58) Field of Classification Search ............... None
See application file for complete search history.

(56) References Cited

U.S. PATENT DOCUMENTS

| 5,356,623 | A | 10/1994 | Von Tersch et al. |
| 5,723,758 | A * | 3/1998 | Payne et al. ............... 800/301 |
| 5,942,658 | A | 8/1999 | Donovan et al. |
| 6,150,589 | A | 11/2000 | Payne et al. |
| 6,369,213 | B1 | 4/2002 | Schnepf et al. |
| 2003/0237111 | A1 | 12/2003 | Baum et al. |

FOREIGN PATENT DOCUMENTS

| EP | 0 193 259 | 9/1986 |
| EP | 0 589 110 | 3/1994 |
| EP | 0 401 979 | 9/1996 |
| EP | 1 099 760 | 5/2001 |
| WO | 94/12264 | 6/1994 |
| WO | 95/04146 | 2/1995 |
| WO | 96/05314 | 2/1996 |
| WO | 98/00546 | 1/1998 |
| WO | 98/26073 | 6/1998 |
| WO | 99/00407 | 1/1999 |
| WO | 99/33991 | 7/1999 |
| WO | 01/19859 | 3/2001 |

OTHER PUBLICATIONS

U.S. Appl. No. 60/153,995, filed Sep. 15, 1999, Baum et al.
Adang et al., Characterized Full-Length and Truncated Plasmid Clones of the Crystal Protein of *Bacillus thuringiensis* subsp. *Kurstaki* HD-73 and Their Toxicity to *Manduca sexta* (1985) Gene 36, 289-300, Elsevier Science Publishers, Amsterdam, Holland.
Bennetzen et al "Codon Selection in Yeast" (1982) J. Biol. Chem. 257, 3026-3031, American Society for Biochemistry and Molecular Biology, Baltimore, MD, USA.
Bernhard et al., "Production of *Bacillus thuringiensis* Insecticides for Experimental and Commercial Uses", in *Bacillus thuringiensis*, an Environmental Biopesticide: Theory and Practice, pp. 255-267, eds. Entwistle, P.F., Cory, J.S., Bailey, M.J. and Higgs, S. John Wiley and Sons, New York (1993).
Christensen et al., "Maize Polyubiquitin Genes: Structure, Thermal Perturbation of Expression and Transcript Splicing, and Promoter Activity Following Transfer to Protoplasts by Electroporation" (1992) Plant Mol. Biol. 18, 675-689, Kluwer Academic Publishers, Belgium.
Cornejo et al., "Activity of a Maize Ubiquitin Promoter in Transgenic Rice",(1993) Plant Mol. Biol. 23, 567-581, Kluwer Academic Publishers, Belgium.
Crickmore et al., "Revision of the Nomenclature for the *Bacillus thuringiensis* Pesticidal Crystal Proteins", (1998) Microbiol. Mol. Biol Rev. 62(3), 807-813, American Society for Microbiology, Washington, D.C.
Datta S. et al,, "Genetically Engineered Fertile Indica-Rice Recovered from Protoplastics", Bio/Technology 8, 736-740 (1990), Nature Publishing, New York NY.
Dulmage, H.T., "Production of Bacteria for Biological Control of Insects" in Biological Control in Crop Production, Ed. Paparizas, D.C., Osmun Publishers, Totowa, NJ, USA, pp. 129-141 (1981).
Finney, Probit Analysis, 3$^{rd}$ Edition, Cambridge University Press (1971) table of contents only.
Franck et al., "Nucleotide Sequence of Cauliflower Mosaic Virus DNA", Cell 21, 285-294 (1980), Cell Press, Cambridge, MA, USA.
French et al., G.G. "Screening cDNA Expression Libraries with Monoclonal and Polyclonal Antibodies Using an Amplified Biotin-Avidin-Peroxidase Technique" Anal. Biochem. 156, 417-423 (1986) Academic Press, Inc., London, UK.
Fromm M., et al., "Inheritance and Expression of Chimeric Genes in the Progeny of Transgenic Maize Plants", Bio/Technology 8, 833-839 (1990), Nature Publishing, New York, NY.
Gardner et al., "The Complete Nucleotide Sequence of an Infectious Clone of Cauliflower Mosaic Virus by M13mp7 Shotgun Sequencing", Nucleic Acids Research 9, 2871-2887 (1981) IRL Press Limited, Oxford, UK.

(Continued)

*Primary Examiner* — Anne Kubelik
(74) *Attorney, Agent, or Firm* — Buchanan Ingersoll & Rooney PC

(57) ABSTRACT

The invention pertains to novel insecticidal compounds derived from *Bacillus thuringiensis* strains. New proteins designated Cry1Jd, Cry9Fa, and Cry1Bf, and insecticidal fragments thereof are provided, as well as DNA sequences encoding these proteins or their insecticidal fragments. Further provided are recombinant hosts expressing such proteins, particularly plant cells and plants.

16 Claims, No Drawings

OTHER PUBLICATIONS

Ge A., et al, "Functional Domains of *Bacillus thuringiensis* Insecticidal Crystal Proteins" J. Biol. Chem. 266 17954-17958 (1991), American Society for Biochemistry and Molecular Biology, Washington, D.C.

Gielen et al., "The Complete Nucleotide Sequence of the TL-DNA of the *Agrobacterium tumefaciens* Plasmid pTiAch5" J., EMBO J. 3, 835-845 (1984) IRL Press Limited, Oxford, England.

Gordon-Kamm W. et al., "Transformation of *Zea mays* L. Using *Agrobacterium tumefaciens* and the Shoot Apex" The Plant Cell 2, 603-618 (1990), American Society of Plant Physiologists, Rockville, MD.

Gould et al., "Transformation of Maize Cells and Regeneration of Fertile Transgenic Plants", Plant Physiol. 95, 426-434 (1991), American Society of Plant Physiologists, Rockville, MD.

Ho et al., "Site-Directed Mutagenesis by Overlap Extension Using the Polymerase Chain Reaction", Gene 77, pp. 51-59, (1989), Elsevier Science Publishers B.V., Amsterdam, Holland.

Hofte et al "Monoclonal Antibody Analysis and Insecticidal Spectrum of Three Types of Lepidopteran-Specific Insecticidal Crystal Proteins of *Bacillus thuringiensis*", Applied and Environmental Microbiology 54, 2010-2017 (1988), American Society for Microbiology, Washington, D.C.

Hofte H. et al., "Insecticidal Crystal Proteins of *Bacillus thuringiensis*", Microbiological Review 53, 242-255 (1989) American Society for Microbiology, Washington, D.C.

Hull et al., "Structure of the Cauliflower Mosaic Virus Genome", Virology 86, 482-493 (1987) Academic Press, Inc. London and New York.

Ishida et al., "High Efficiency Transformation of Maize (*Zea mays* L.) Mediated by *Agrobacterium tumefaciens*" Nature Biotechnology 14, 745-750, (1996), Nature America, New York.

Itakura et al., "Expression in *Escherichia coli* of a Chemically Synthesized Gene for the Hormone Somatostatin" (1977) Science 198, 1056-1063, American Assn for the Advancement of Science, Washington, D.C.

Jansens et al. "Transgenic Corn Expressing a Cry9C Insecticidal Protein from *Bacillus thuringiensis* Protected from European Corn Borer Damage", Crop Science 37, 1616-1624, (1997), Crop Science Society of America, Madison Wisconsin.

Kumar et al., "The Insecticidal Proteins of *Bacillus thuringiensis*", Microbiology, 1996, vol. 42, pp. 1-43.

Lambert B., "*Bacillus thuringiensis* Encoding Crystal Protein", Accession No. Z22512, Apr. 8, 1993, abstract.

Last et al., "pEmu: an Improved Promoter for Gene Expression in Cereal Cells", Theor. Appl. Genet. 81, 581-588, (1990), Springer, Berlin and New York.

Lereclus et al., "Expansion of Insecticidal Host Range of *Bacillus thuringiensis* by in vivo Genetic Recombination", Bio/Technology 10, 418 (1992) Nature Publishing Co., New York.

Mahillon et al., "Transformation of *Bacillus thuringiensis* by Electroporation", FEMS Microbial. Letters 60, 205-210 (1989) Elsevier, Amsterdam, Holland.

Maxam et al., "Sequencing End-Labeled DNA with Base-Specific Chemical Cleavages", Methods in Enzymol. 65, 499-560 (1980), Academic Press, Inc., London, U.K.

McBride et al., "Amplification of a Chimeric *Bacillus* Gene in Chloroplasts Leads to an Extraordinary Level of an Insecticidal Protein in Tobacco", 1995, Bio/Technology 13, 362, Nature Publishing Co., New York.

Murray E. et al., "Codon Usage in Plant Genes", Nucleic Acids Research 17(2), 477-498 (1989), Oxford Univ. Press, Oxford, England.

Peferoen., "*Bacillus thuringiensis* CryID Gene for Insecticidal Crystal Protein (Lepidoptera Specific)", Accession No. X54160, Oct. 5, 1990, abstract.

Sanger et al., "DNA Sequencing with Chain-Terminating Inhibitors", Proc. Natl. Sci. USA 74(12), 5463-5467 (1977), National Academy of Sciences, Washington, D.C.

Schnepf et al., "The Amino Acid Sequence of a Crystal Protein from *Bacillus thuringiensis* Deduced from the DNA Base Sequence", (1985) Journal of Biological Chemistry 260, 6264, American Society of Biological Chemists, Inc., U.S.A.

Schnepf et al., "*Bacillus thuringiensis* and Its Pesticidal Crystal Protein", Microbiology and Molecular Biology Reviews, 1998, vol. 62, No. 3, pp. 775-806, American Society for Microbiology, Washington, D.C.

Shevelev et al., "*Bacillus thuringiensis* CryIX Gene for Delta-Endotoxin", Accession No. X75019, Dec. 23, 1993, abstract.

Shimamoto K., et al., "Fertile Transgenic Rice Plants Regenerated from Transformed Protoplasts", Nature 338, 274-276 (1989), Nature Publishing Group, London, England.

Stanssens P. et al, "Efficient Oligonucleotide-Directed Construction of Mutations in Expression Vectors by the Gapped Duplex DNA method Using Alternating Selectable Markers", Nucleic Acids Research 12, 4441-4454 (1989), IRL Press, Oxford, England.

Vaeck M., et al., "Transgenic Plants Protected from Insect Attack", Nature, vol. 328 (1987), pp. 33-37, Nature Publishing Group, London, England.

Vanderzant et al., "Rearing of the Bollworm on Artificial Diet", Journal of Economic Entomology, vol. 55, No. 1, (1962) pp. 140-141, Entomological Society of America, College Park, MD.

Van Rie et al., "Mechanism of Insect Resistance to the Microbial Insecticide *Bacillus thuringiensis*", Science 247, 72 (1990), American Assn for the Advancement of Science, Washington, D.C.

Velten, J., et al., "Isolation of a Dual Plant Promoter Fragment from the Ti Plasmid of *Agrobacterium tumefaciens*", EMBO J. 3, 2723-2730 (1984), IRL Press Limited, Oxford, England.

Velten, J. et al., "Selection-Expression Plasmid Vectors for Use in Genetic Transformation of Higher Plants", (1985), pp. 6981-6999, Nucleic Acids Research, IRL Press, Oxford, England.

Visser, B., et al., "Domain-Structure Studies of *Bacillus thuringiensis* Crystal Proteins: A Genetic Approach", in *Bacillus thuringiensis*, an Environmental Biopesticide: Theory and Practice, pp. 71-88, eds. Entwistle, P.F., Cory, J.S. Bailey, M.J. and Higgs, S., John Wiley and Sons, New York (1993).

Wada et al., "codon Usage Tabulated from the GenBank Genetic Sequence Data", (1990) Nucl. Acids Res. 18, 2367-1411, Oxford University Press, Oxford, England.

Wasano et al., "*Bacillus thuringiensis* Delta-Endotoxin Gene, Partial cds", Accession No. AF093107, Oct. 8, 1998, abstract.

White et al., "The Polymerase Chain Reaction", TIG (1989), vol. 5, No. 6, pp. 185-189, Elsevier Science Publishers, UK.

Yannisch-Perron, C. et al., "Improved M13 Phage Cloning Vectors and Host Strains: Nucleotide Sequences of the M13mp18 and pUC19 Vectors", Gene 33, 103-119 (1985) Elsevier Science Publishers, UK.

Zhang et al., "analysis of Rice *Act1* 5' Region Activity in Transgenic Rice Plants" (1991) The Plant Cell 3, 1155-1165, American Society of Plant Physiologists, Rockville, MD.

* cited by examiner

INSECTICIDAL PROTEINS FROM *BACILLUS THURINGIENSIS*

CROSS REFERENCE TO RELATED APPLICATIONS

This application is a divisional application of U.S. patent application Ser. No. 12/081,208, filed Apr. 11, 2008, which is a divisional of U.S. application Ser. No. 11/600,831, filed Nov. 17, 2006, now U.S. Pat. No. 7,361,808, which is a divisional of U.S. application Ser. No: 10/614,524, filed Jul. 8, 2003, now U.S. Pat. No. 7,169,971, which is a continuation of U.S. application Ser. No: 09/739,243, filed Dec. 19, 2000, which claims the benefit of U.S. Ser. No. 60/173,387, filed Dec. 28, 1999, each of which are incorporated herein by reference in its entirety for all purposes.

INTRODUCTION

The present invention relates to new DNA sequences encoding insecticidal proteins produced by *Bacillus thuringiensis* strains. Particularly, new DNA sequences encoding proteins designated as Cry9Fa, Cry1Jd, and Cry1Bf are provided which are useful to protect plants from insect damage. Also included herein are micro-organisms and plants transformed with at least one of the newly isolated genes so that they are useful to confer insect resistance by expression of insecticidal protein.

BACKGROUND OF THE INVENTION (i) Field of the Invention:

Bt or *Bacillus thuringiensis* is well known for its specific toxicity to insect pests, and has been used since almost a century to control insect pests of plants. In more recent years, transgenic plants expressing Bt proteins were made which were found to successfully control insect damage on plants (e.g., Vaeck et al., 1987).

Despite the isolation of a number of Bt crystal protein genes, the search for new genes encoding insecticidal proteins continues. Indeed, insecticidal Bt crystal proteins are known to have a relatively narrow target insect range compared to chemical insecticides. Also, having multiple toxins active on the same target insect species allows the use of proteins having different modes of action so that insect resistance development can be prevented or delayed.

(ii) Description of Related Art:

Previously, several types of Cry1B-, Cry1J-, and Cry9-proteins were identified (see Crickmore et al., 1998, incorporated herein by reference, for all details).

The new Cry1Bf protein has the closest sequence identity with the Cry1Be protein (Payne et al, 1998, U.S. Pat. No. 5,723,758), but still differs in about 14 percent of the amino add sequence of its toxic protein fragment with the toxic fragment of the Cry1Be protein. The closest sequence identity with the Cry1Jd toxic fragment was found in the toxic fragment of the Cry1Jc1 protein (U.S. Pat. No. 5,723,758), but the toxic fragments of both proteins still differ in about 18% of their amino acid sequence.

The closest sequence identity with the Cry9Fa toxic fragment was found with the toxic fragment of the Cry9Ea1 protein as described by Midoh et al. (PCT Patent publication WO 98/26073) and Narva et al. (PCT patent publication WO 98/00546), but the toxic fragments of the Cry9Fa and Cry9Ea proteins still differ in about 21% of their amino acid sequence.

SUMMARY OF THE INVENTION

In accordance with this invention is provided a DNA sequence encoding a protein comprising the amino acid sequence selected from the group consisting of: a) the amino acid sequence of the insecticidal trypsin-digestion fragment of the protein encoded by the cry1Bf gene deposited at the BCCM-LMBP under accession number LMBP 3986, b) the amino acid sequence of the insecticidal trypsin-digestion fragment of the protein encoded by the cry1Jd gene deposited at the BCCM-LMBP under accession number LMBP 3983, and c) the amino acid sequence of the insecticidal trypsin-digestion fragment of the protein encoded by the cry9Fa gene deposited at the BCCM-LMBP under accession number LMBP 3984.

Particularly preferred in accordance with this invention is a DNA sequence encoding a protein comprising the amino acid sequence selected from the group consisting of: the amino acid sequence of an insecticidal fragment of the protein of SEQ ID No. 2, the amino acid sequence of an insecticidal fragment of the protein of SEQ ID No. 4, and the amino acid sequence of an insecticidal fragment of the protein of SEQ ID No. 6; alternatively, a DNA encoding a protein comprising the amino acid sequence of the group selected from: the amino acid sequence of SEQ ID No. 2, the amino acid sequence of SEQ ID No. 4, the amino acid sequence of SEQ ID No. 6; or a DNA sequence comprising the DNA sequence of SEQ ID No. 1, SEQ ID No. 3, or SEQ ID No. 5.

Further, in accordance with this invention are provided DNA sequences encoding at least the following portions of the newly-isolated proteins: the amino acid sequence of SEQ ID No. 2 from amino acid position 1 to amino acid position 640, the amino acid sequence of SEQ ID No. 4 from amino acid position 1 to amino acid position 596, and the amino acid sequence of SEQ ID No. 6 from amino acid position 1 to amino acid position 652.

Further, in accordance with this invention are provided the above DNA sequences comprising an artificial DNA sequence having a different codon usage compared to the naturally occurring DNA sequence but encoding the same protein or its insecticidal fragment.

Even further provided in accordance with this invention is a protein comprising the amino acid sequence selected from the group consisting of: a) the amino acid sequence of the insecticidal trypsin-digestion fragment of the protein encoded by the cry1Bf gene deposited at the BCCM-LMBP under accession number LMBP 3986, b) the amino acid sequence of the insecticidal trypsin-digestion fragment of the protein encoded by the cry1Jd gene deposited at the BCCM-LMBP under accession number LMBP 3983, and c) the amino acid sequence of the insecticidal trypsin-digestion fragment of the protein encoded by the cry9Fa gene deposited at the BCCM-LMBP under accession number LMBP 3984.

Particularly preferred herein is a protein comprising the amino acid sequence selected from the group consisting of: the amino acid sequence of an insecticidal fragment of the protein of SEQ ID No. 2, the amino acid sequence of an insecticidal fragment of the protein of SEQ ID No. 4, and the amino acid sequence of an insecticidal fragment of the protein of SEQ ID No. 6; alternatively a protein, comprising the amino acid sequence selected from the group consisting of: the amino acid sequence of SEQ ID No. 2 from amino acid position 1 to amino acid position 640, the amino acid sequence of SEQ ID No. 4 from amino acid position 1 to amino acid position 596, and the amino acid sequence of SEQ ID No. 6 from amino acid position 1 to amino acid position 652; or a protein comprising the amino acid sequence of SEQ ID No. 2, SEQ ID No. 4, or SEQ ID No. 6.

Also provided herein are chimeric genes comprising the DNA as defined above under the control of a plant-expressible promoter, and plant cells, plants or seeds transformed to contain those chimeric genes, particularly plant cells, plants, or seeds selected from the group consisting of: corn, cotton, rice, oilseed rape, Brassica species, eggplant, soybean, potato, sunflower, tomato, sugarcane, tea, beans, tobacco, strawberry, clover, cucumber, watermelon, pepper, oat, barley, wheat, dahlia, gladiolus, chrysanthemum, sugarbeet, sorghum, alfalfa, and peanut. In accordance with this invention, the chimeric gene can be integrated in the nuclear or chloroplast DNA of the plant cells.

Further in accordance with this invention are provided micro-organisms, transformed to contain any of the above DNA sequences, particularly those selected from the genus *Agrobacterium, Escherichia*, or *Bacillus*.

Also provided herein is a process for controlling insects, comprising expressing any of the above DNA sequences in a host cell, particularly plant cells, and contacting insects with said host cells, and a process for rendering a plant resistant to insects, comprising transforming plants cells with any of the above DNA sequences or chimeric genes, and regenerating transformed plants from such cells which are resistant to insects.

DETAILED DESCRIPTION OF PREFERRED EMBODIMENTS

In accordance with this invention, DNA sequences encoding new Bt toxins have been isolated and characterized. The new genes were designated cry1Bf, cry1Jd and cry9Fa, and their encoded proteins Cry1Bf, Cry1Jd and Cry9Fa.

in accordance with this invention "Cry1Bf protein" refers to any protein comprising the smallest protein fragment of the amino acid sequence of SEQ ID No. 2 which retains insecticidal activity, particularly any protein comprising the amino acid sequence from the amino acid at position 1 to the amino acid at position 640 in SEQ ID No. 2, including but not limited to the complete protein with the amino acid sequence of SEQ ID No. 2. This includes hybrids or chimeric proteins comprising the smallest toxic protein fragment, as well as proteins containing at least one of the three functional domains of the toxic fragment of SEQ ID No. 2. The term "DNA/protein comprising the sequence X", as used herein, refers to a DNA or protein including or containing at least the sequence X, so that other nucleotide or amino acid sequences can be included at the 5' (or N-terminal) and/or 3' (or C-terminal) end, e.g. (the nucleotide sequence of) a selectable marker protein as disclosed in EP 0 193 259.

In accordance with this invention, "Cry9Fa protein" or "Cry9F protein" refers to any protein comprising the smallest protein fragment of the amino acid sequence of SEQ ID No. 6 which retains insecticidal activity, particularly any protein comprising the amino acid sequence from the amino acid, at position 1 to the amino acid at position 652 in SEQ ID No. 6, including but not limited to the complete protein with the amino acid sequence of SEQ ID No. 6. This includes hybrids or chimeric proteins comprising the smallest toxic protein fragment, as well as proteins containing at least one of the three functional domains of the toxic fragment of SEQ ID No. 6.

In accordance with this invention, "Cry1Jd protein" refers to any protein comprising the smallest protein fragment of the amino acid sequence of SEQ ID No. 4 which retains insecticidal activity, particularly any protein comprising the amino acid sequence from the amino acid at position 1 to the amino acid at position 596 in SEQ ID No. 4, including but not limited to the complete protein with the amino acid sequence of SEQ ID No. 4. This includes hybrids or chimeric proteins comprising the smallest toxic protein fragment, as well as proteins containing at least one of the three functional domains of the toxic fragment of SEQ ID No. 4.

As used herein, the terms "cry1Bf DNA", "cry9Fa DNA", or "cry1Jd DNA", refer to any DNA sequence encoding the Cry1Bf, Cry9Fa, or Cry1Jd protein, respectively, as defined above. This includes naturally occurring, artificial or synthetic DNA sequences encoding the newly isolated proteins or their insecticidal fragments as defined above. Also included herein are DNA sequences encoding insecticidal proteins which are similar enough to the coding regions of the genomic DNA sequences deposited or the sequences provided in the sequence listing so that they can (i.e., have the ability to) hybridize to these DNA sequences under stringent hybridization conditions. Stringent hybridization conditions, as used herein, refers particularly to the following conditions: immobilizing the relevant genomic DNA sequences on a filter, and prehybridizing the filters for either 1 to 2 hours in 50% formamide, 5% SSPE, 2×Denhardt's reagent and 0.1% SDS at 42° C. or 1 to 2 hours in 6×SSC, 2×Denhardt's reagent and 0.1% SDS at 68° C. The denatured labeled probe is then added directly to the prehybridization fluid and incubation is carried out for 16 to 24 hours at the appropriate temperature mentioned above. After incubation, the filters are then washed for 20 minutes at room temperature in 1×SSC, 0.1% SDS, followed by three washes of 20 minutes each at 68° C. in 0.2×SSC and 0.1% SDS. An autoradiograph is established by exposing the filters for 24 to 48 hours to X-ray film (Kodak XAR-2 or equivalent) at −70° C. with an intensifying screen. Of course, equivalent conditions and parameters can be used in this process while still retaining the desired stringent hybridization conditions. One of such equivalent conditions includes: immobilizing the relevant genomic DNA sequences on a filter, and prehybridizing the filters for either 1 to 2 hours in 50% formamide, 5% SSPE, 2×Denhardt's reagent and 0.1% SDS at 42° C. or 1 to 2 hours in 6×SSC, 2×Denhardt's reagent and 0.1% SDS at 68° C. The denatured (dig- or radio-)labeled probe is then added directly to the prehybridization fluid and incubation is carried out for 16 to 24 hours at the appropriate temperature mentioned above. After incubation, the filters are then washed for 30 minutes at room temperature in 2×SSC, 0.1% SDS, followed by 2 washes of 30 minutes each at 68° C. in 0.5×SSC and 0.1% SDS. An autoradiograph is established by exposing the filters for 24 to 48 hours to X-ray film (Kodak XAR-2 or equivalent) at −70° C. with an intensifying screen "Insecticidal activity" of a protein, as used herein, means the capacity of a protein to kill insects when such protein is fed to insects, preferably by expression in a recombinant host such as a plant. "Insect-controlling amounts" of a protein, as used herein, refers to an amount of protein which is sufficient to limit damage on a plant by insects feeding on such plant to commercially acceptable levels, e.g. by killing the insects or by inhibiting the insect development or growth in such a manner that they provide less damage to a plant and plant yield is not significantly adversely affected.

In accordance with this invention, insects susceptible to the new Cry proteins of the invention are contacted with this protein in insect-controlling amounts, preferably insecticidal amounts.

"Cry protein" or "Cry protein of this invention", as used herein, refers to any one of the new proteins isolated in accordance with this invention and identified herein as Cry1Bf, Cry9Fa, or Cry1Jd protein. A Cry protein, as used herein, can be a protein in the full length size, also named a protoxin, or can be in a slightly or fully (e.g., N- and C-terminal truncation) truncated form as long as the insecticidal activity is retained, or can be a combination of different proteins or protein parts in a hybrid or fusion protein. A "Cry protoxin" refers to the full length crystal protein as it is encoded by the naturally-occurring Bt DNA sequence, a "Cry toxin" refers to an insecticidal fragment thereof, particularly the smallest toxic fragment thereof, typically in the molecular weight range of about 60 to about 80 kD as determined by SDS-PAGE electrophoresis. A "cry gene" or "cry DNA", as used herein, is a DNA sequence encoding a Cry protein in accordance with this invention, referring to any of the cry1Bf, cry9Fa, and cry1Jd DNA sequences defined above.

The "smallest toxic fragment" of a Cry protein, as used herein, is that fragment as can be obtained by trypsin or chymotrypsin digestion of the full length solubilized crystal protein that retains toxicity, or that toxic protein fragment encoded by DNA fragments of the Cry protein. This protein will mostly have a short N-terminal and a long C-terminal truncation compared to the protoxin. Although for recombinant expression, toxic fragments starting at or around original amino acid position 1 are a more preferred embodiment in accordance with this invention, it should be noted that besides a C-terminal truncation, some N-terminal amino acids can also be deleted while retaining the insecticidal character of the protein. The N-terminal end of the smallest toxic fragment is conveniently determined by N-terminal amino acid sequence determination of trypsin- or chymotrypsin-treated soluble crystal protein by techniques routinely available in the art.

Dna encoding the Cry proteins of this invention can be isolated in a conventional manner from the *E. coli* strains, deposited on Nov. 25, 1999 at the BCCM-LMBP under accession numbers LMBP 3983, LMBP 3984, LMBP 3985 and LMBP 3986. The encoded Cry proteins can be used to prepare specific monoclonal or polyclonal antibodies in a conventional manner (Höfte et al., 1988). The toxin forms can be obtained by protease (e.g., trypsin) digestion of the Cry protoxins.

The DNA sequences encoding the Cry proteins can be isolated in a conventional manner from the respective strains or can be synthesized based on the encoded amino acid sequence.

The DNA sequences encoding the Cry proteins of the invention were identified by digesting total DNA from isolated Bt strains with restriction enzymes; size fractionating the DNA fragments, so produced, into DNA fractions of 5 to 10 Kb; ligating these fractions to cloning vectors; screening the *E. coli*, transformed with the cloning vectors, with a DNA probe that was constructed from a region of known Bt crystal protein genes or with a DNA probe based on specific PCR fragments generated from Bt DNA using primers corresponding to known Bt crystal protein genes.

Also, DNA sequences for use in this invention can be made synthetically. Indeed, because of the degeneracy of the genetic code, some amino acid codons can be replaced with others without changing the amino acid sequence of the protein. Furthermore, some amino acids can be substituted by other equivalent amino acids without significantly changing the insecticidal activity of the protein. Also, changes in amino acid sequence or composition in regions of the molecule, different from those responsible for binding and toxicity (e.g.; pore formation) are less likely to cause a difference in insecticidal activity of the protein. Such equivalents of the gene include DNA sequences hybridizing to the DNA sequence of the Cry toxins or protoxins of SEQ ID. No. 2, 4, or 6 under stringent conditions and encoding a protein with the same insecticidal characteristics as the (pro)toxin of this invention, or DNA sequences encoding proteins with an amino acid sequence identity of at least 85%, preferably at least 90%, most preferably at least 95%, with the protein toxin form (from the N-terminus to 2 amino acids beyond conserved sequence block 5 as defined in Schnepf et al., 1998) or with the protein protoxin form of the Cry1Bf, Cry9FA or Cry1Jd proteins of this invention, as determined using the GAP program of the Wisconsin package of GCG (Madison, Wis., USA, version 10.0; GCG defaults were used within the GAP program; for the amino acid sequence comparisons, the blosum62 scoring matrix was used).

Of course, any other DNA sequence differing in its codon usage but encoding the same protein or a similar protein with substantially the same insecticidal activity, can be constructed, depending on the particular purpose. It has been described in prokaryotic and eucaryotic expression systems that changing the codon usage to that of the host cell is desired for gene expression in foreign hosts (Bennetzen & Hall, 1982; Itakura, 1977). Furthermore, Bt crystal protein genes are known to have no bias towards eucaryotic codons, and to be very AT-rich (Adang et al., 1985, Schnepf et al., 1985). Codon usage tables are available in the literature (Wada et al., 1990; Murray et al., 1989) and in the major DNA sequence databanks (e.g. EMBL at Heidelberg, Germany). Accordingly, synthetic DNA sequences can be constructed so that the same or substantially the same proteins are produced. It is evident that several DNA sequences can be devised once the amino acid sequence of the Cry proteins of this invention is known. Such other DNA sequences include synthetic or semi-synthetic DNA sequences that have been changed in order to inactivate certain sites in the gene, e.g. by selectively inactivating certain cryptic regulatory or processing elements present in the native sequence as described in PCT publications WO 91/16432 and WO 93/09218, or by adapting the overall codon usage to that of a more related host organism, preferably that of the host organism in which expression is desired. When making such genes, the encoded amino acid sequence should be retained to the maximum extent possible, although truncations or minor replacements or additions of amino acids can be done as long as the toxicity of the protein is not negatively affected.

Small modifications to a DNA sequence such as described above can be routinely made by PCR-mediated mutagenesis (Ho et al., 1989, White et al., 1989).

With the term "substantially the same", when referring to a protein, is meant to include a protein that differs in some amino acids, or has some amino acids added (e.g. a fusion protein, see Vaeck et al., 1987) or deleted (e.g. N- or C-terminal truncation), as long as the protein has no major difference in its insecticidal activity.

The term "functional domain" of a Cry toxin as used herein means any part(s) or domain(s) of the toxin with a specific structure that can be transferred to another (Cry) protein for providing a new hybrid protein with at least one functional characteristic (e.g., the binding and/or toxicity characteristics) of the Cry toxin of the invention (Ge et al., 1991). Such parts can form an essential feature of the hybrid Bt protein with the binding and/or toxicity characteristics of the Cry protein of this invention. Such a hybrid protein can have an enlarged host range, an improved toxicity and/or can be used in a strategy to prevent insect resistance development (European Patent Publication ("EP") 408 403; Visser et al., 1993).

The 5 to 10 Kb fragments, prepared from total DNA of the Bt strains of the invention, can be ligated in suitable expression vectors and transformed in *E. coli*, and the clones can then be screened by conventional colony immunoprobing methods (French et al., 1986) for expression of the toxin with monoclonal or polyclonal antibodies raised against the Cry proteins, or by hybridization with DNA probes.

Also/the 5 to 10 Kb fragments, prepared from total DNA of the Bt strains of the invention or fragments thereof cloned and/or subcloned in *E. coli*, can be ligated in suitable Bt shuttle vectors (Lereclus et al., 1992) and transformed in a crystal minus Bt-mutant. The clones are then screened for production of crystals (detected by microscopy) or crystal proteins (detected by SDS-PAGE).

The genes encoding the Cry proteins of this invention can be sequenced in a conventional manner (Maxam and Gilbert, 1980; Sanger, 1977) to obtain the DNA sequence. Sequence comparisons indicated that the genes are different from previously described genes encoding protoxins and toxins with activity against Lepidoptera (Höfte and Whiteley, 1989; Crickmore, et al., 1998); and the Dec. 15, 1999 and Oct. 16, 2000 updates on the Bt nomenclature website corresponding to the Crickmore et al. (1998) publication, found at:

http://epunix.biols.susx.ac.uk/Home/Neil_Crickmore/Bt/index.html

An insecticidally effective part of the DNA sequences, encoding an insecticidally effective portion of the newly identified Cry protein protoxin forms, can be made in a conventional manner after sequence analysis of the gene. In such fragments, it is preferred that at least the sequence up to the C-terminal end of conserved sequence block 5 of Bt proteins (Hofte & Whiteley, 1989; Schnepf et al., 1998), preferably up to two amino acids C-terminal of the conserved sequence block 5, is retained. The amino acid sequence of the Cry proteins can be determined from the DNA sequence of the isolated DNA sequences. By "an insecticidally effective part" of DNA sequences encoding the Cry protein, also referred to herein as "truncated gene" or "truncated DNA", is meant a DNA sequence encoding a polypeptide which has fewer amino acids than the Cry protein protoxin form but which is insecticidal to insects.

In order to express all or an insecticidally effective part of the DNA sequence encoding a Cry protein of this invention in *E. coli*, in other Bt strains and in plants, suitable restriction sites can be introduced, flanking the DNA sequence. This can be done by site-directed mutagenesis, using well-known procedures (Stanssens et al., 1989; White et al., 1989). In order to obtain improved expression in plants, the codon usage of the cry gene or insecticidally effective cry gene part of this invention can be modified to form an equivalent, modified or artificial gene or gene part in accordance with PCT publications WO 91/16432 and WO 93/09218; EP 0 358 962 and EP 0 359 472, or the Bt genes or gene parts can be inserted in the chloroplast genome and expressed there using a chloropast-active promoter (e.g., Mc Bride et al., 1995). For obtaining enhanced expression in monocot plants such as corn, a monocot intron also can be added to the chimeric gene, and the DNA sequence of the cry gene or its insecticidal part of this invention can be further changed in a translationally neutral manner, to modify possibly inhibiting DNA sequences present in the gene part by means of site-directed intron insertion and/or by introducing changes to the codon usage, e.g., adapting the codon usage to that most preferred by the specific plant (Murray et al., 1989) without changing significantly the encoded amino acid sequence.

Furthermore, the binding properties of the Cry proteins of the invention can be evaluated, using methods known in the art (Van Rie et al., 1990), to determine if the Cry proteins of the invention bind to sites on the insect midgut that are different from those recognized by other, known Cry or other Bt proteins. Bt toxins with different binding sites in relevant susceptible insects are very valuable to replace known Bt toxins to which insects may have developed resistance, or to use in combination with Bt toxins having a different mode of action to prevent or delay the development of insect resistance against Bt toxins, particularly when expressed in a plant. Because of the characteristics of the newly isolated Bt toxins, they are extremely useful for transforming plants, e.g. monocots such as corn or rice and vegetables such as *Brassica* species plants, to protect these plants from insect damage.

The insecticidally effective cry gene part or its equivalent, preferably the cry chimeric gene, encoding an insecticidally effective portion of the Cry protoxin, can be stably inserted in a conventional manner into the nuclear genome of a single plant cell, and the so-transformed plant cell can be used in a conventional manner to produce a transformed plant that is insect-resistant. In this regard, a disarmed Ti-plasmid, containing the insecticidally effective cry gene part, in *Agrobacterium tumefaciens* can be used to transform the plant cell, and thereafter, a transformed plant can be regenerated from the transformed plant cell using the procedures described, for example, in EP 0 116 718, EP 0 270 822, PCT publication WO 84/02913 and published European Patent application ("EP") 0 242 246 and in Gould et al. (1991). Preferred Ti-plasmid vectors each contain the insecticidally effective cry gene part between the border sequences, or at least located to the left of the right border sequence, of the T-DNA of the Ti-plasmid. Of course, other types of vectors can be used to transform the plant cell, using procedures such as direct gene transfer (as described, for example in EP 0 233 247), pollen mediated transformation (as described, for example in EP 0 270 356, PCT publication WO 85/01856, and U.S. Pat. No. 4,684,611), plant RNA virus-mediated transformation (as described, for example in EP 0 067 553 and U.S. Pat. No. 4,407,956), liposome-mediated transformation (as described, for example in U.S. Pat. No. 4,536,475), and other methods such as the recently described methods for transforming certain lines of corn (Fromm et al., 1990; Gordon-Kamm et al., 1990) and rice (Shimamoto et al., 1989; Datta et al., 1990) and the recently described method for transforming monocots generally (PCT publication WO 92/09696).

The resulting transformed plant can be used in a conventional plant breeding scheme to produce more transformed plants with the same characteristics or to introduce the insecticidally effective cry gene part in other varieties of the same or related plant species. Seeds, which are obtained from the transformed plants, contain the insecticidally effective cry gene part as a stable genomic insert. Cells of the transformed plant can be cultured in a conventional manner to produce the insecticidally effective portion of the Cry protoxin, preferably the Cry toxin, which can be recovered for use in conventional insecticide compositions against Lepidoptera (U.S. Pat. No. 5,254,799). In accordance with this invention, plants or seeds of the invention can be used to obtain resistance to insects, e.g. by sowing or planting in a field wherein damaging insects usually occur, said seeds or plants. Methods for obtaining insect resistance and methods for obtaining improved yield or reduced insect damage are thus provided in accordance with the invention by planting or sowing in a field, preferably a field wherein damaging insects feeding on such plants usually occur or are expected to occur at levels which provide economic damage to the plants, the plants of seeds of the invention producing the Cry proteins of the invention.

The insecticidally effective cry gene part, preferably the truncated cry gene, is inserted in a plant cell genome so that the inserted gene is downstream (i.e. 3') of, and under the control of, a promoter which can direct the expression of the gene part in the plant cell. This is preferably accomplished by inserting the cry chimeric gene in the plant cell genome, particularly in the nuclear or chloroplast genome. Preferred promoters include: the strong constitutive 35S promoters (the "35S promoters") of the cauliflower mosaic virus (CaMV) of isolates CM 1841 (Gardner et al., 1981), CabbB-S (Franck et al., 1980) and CabbB-JI (Hull and Howell, 1987); promoters from the ubiquitin family (e.g., the maize ubiquitin promoter of Christensen et al., 1992, see also Cornejo et al., 1993), the gos2 promoter (de Pater et al., 1992), the emu promoter (Last et al., 1990), rice actin promoters such as the promoter described by Zhang et al. (1991); and the TR1' promoter and the TR2' promoter (the "TR1 promoter" and "TR2' promoter", respectively) which drive the expression of the 1' and 2' genes, respectively, of the T-DNA (Velten et al., 1984). Alternatively, a promoter can be utilized which is not constitutive but rather is specific for one or more tissues or organs of the plant (e.g., leaves and/or roots) whereby the inserted cry gene part is expressed only in cells of the specific tissue(s) or organ(s). For example, the insecticidally effective cry gene part could be selectively expressed in the leaves of a plant (e.g., corn, cotton) by placing the insecticidally effective gene part under the control of a light-inducible promoter such as the promoter of the ribulose-1,5-bisphosphate carboxylase small subunit gene of the plant itself or of another plant such as pea as disclosed in U.S. Pat. No. 5,254,799. Another alternative is to use a promoter whose expression is inducible (e.g., by temperature, wounding or chemical factors).

The insecticidally effective cry gene part is inserted in the plant genome so that the inserted gene part is upstream (i.e., 5') of suitable 3' end transcription regulation signals (i.e., transcript formation and polyadenylation signals). This is preferably accomplished by inserting the cry chimeric gene in the plant cell genome. Preferred polyadenylation and transcript formation signals include those of the octopine synthase gene (Gielen et al., 1984) and the T-DNA gene 7 (Velten and Schell, 1985), which act as 3'-untranslated DNA sequences in transformed plant cells.

The insecticidally effective cry gene part can optionally be inserted in the plant genome as a hybrid gene (U.S. Pat. No. 5,254,799; Vaeck et al., 1987) under the control of the same promoter as a selectable marker gene, such as the neo gene (EP 0 242 236) encoding kanamycin resistance, so that the plant expresses a fusion protein.

All or part of the cry gene, encoding an anti-lepidopteran protein, can also be used to transform other bacteria, such as a *B. thuringiensis* which has insecticidal activity against Lepidoptera or Coleoptera. Thereby, a transformed Bt strain can be produced which is useful for combatting a wide spectrum of lepidopteran and coleopteran insect pests or for combatting additional lepidopteran insect pests. Transformation of bacteria, such as bacteria of the genus *Agrobacterium, Bacillus* or *Escherichia*, with all or part of the cry gene of this invention, incorporated in a suitable cloning vehicle, can be carried out in a conventional manner, preferably using conventional electroporation techniques as described in Mahillon et al. (1989) and in PCT Patent publication WO 90/06999.

Transformed *Bacillus* species strains containing the cry gene of this invention can be fermented by conventional methods (Dulmage, 1981; Bernhard and Utz, 1993) to provide high yields of cells. Under appropriate conditions which are well understood (Dulmage, 1981), these strains each sporulate to produce crystal proteins containing the Cry protoxin in high yields.

An insecticidal, particularly anti-lepidopteran, composition of this invention can be formulated in a conventional manner using the microorganisms transformed with the cry gene, or preferably their respective Cry proteins or the Cry protoxin, toxin or insecticidally effective protoxin portion as an active ingredient, together with suitable carriers, diluents, emulsifiers and/or dispersants (e.g., as described by Bernhard and Utz, 1993). This insecticide composition can be formulated as a wettable powder, pellets, granules or dust or as a liquid formulation with aqueous or non-aqueous solvents as a foam, gel, suspension, concentrate, etc.

A method for controlling insects, particularly Lepidoptera, in accordance with this invention can comprise applying (e.g., spraying), to a locus (area) to be protected, an insecticidal amount of the Cry proteins or host cells transformed with the cry gene of this invention. The locus to be protected can include, for example, the habitat of the insect pests or growing vegetation or an area where vegetation is to be grown.

To obtain the Cry protoxin or toxin, cells of the recombinant hosts expressing the Cry protein can be grown in a conventional manner on a suitable culture medium and then lysed using conventional means such as enzymatic degradation or detergents or the like. The protoxin can then be separated and purified by standard techniques such as chromatography, extraction, electrophoresis, or the like. The toxin can then be obtained by trypsin digestion of the protoxin.

The following Examples illustrate the invention, and are not provided to limit the invention or the protection sought. The sequence listing referred to in the Examples, the Claims and the Description is as follows:

Sequence Listing:
SEQ ID No. 1—amino acid and DNA sequence of Cry1Bf protein and DNA
SEQ ID No. 2—amino acid sequence of Cry1Bf protein.
SEQ ID No. 3—amino acid and DNA sequence of Cry1Jd protein and DNA.
SEQ ID No. 4—amino acid sequence Cry1Jd protein.
SEQ ID No. 5—amino acid and DNA sequence of Cry9Fa protein and DNA.
SEQ ID No 6—amino acid sequence of Cry9Fa protein.
SEQ ID No. 7—DNA sequence for primer Cry1B.fw.
SEQ ID No. 8—DNA sequence for primer B.R.
SEQ ID No. 9—DNA sequence for primer B.F.
SEQ ID No. 10—DNA sequence for primer JFW.
SEQ ID No. 11—DNA sequence for primer JRV.
SEQ ID No. 12—DNA sequence for primer 9FW.
SEQ ID No. 13—DNA sequence for primer 9RV.

Unless otherwise stated in the Examples, all procedures for making and manipulating recombinant DNA are carried out by the standard procedures described in Sambrook et al., Molecular Cloning—A Laboratory Manual, Second Ed., Cold Spring Harbor Laboratory Press, NY (1989), and in Volumes 1 and 2 of Ausubel et al. (1994) Current Protocols in Molecular Biology, Current Protocols, USA. Standard materials and methods for plant molecular biology work are described in Plant Molecular Biology Labfax (1993) by R. R. D. Croy, jointly published by BIOS Scientific Publications Ltd (UK) and Blackwell Scientific Publications (UK). Procedures for PCR technology can be found in "PCR protocols: a guide to methods and applications", Edited by M. A. Innis, D. H. Gelfand, J. J. Sninsky and T. J. White (Academic Press, Inc., 1990).

EXAMPLES

Example 1

Characterization of the Strains

The BtS02072BG strain was isolated from a grain dust sample collected in Santo Tomas la Union, Ilocos, Philippines. The BtS02739C strain was isolated from a grain dust sample collected in Lucena City, South Tagalog, Philippines.

Each strain can be cultivated on conventional standard media, preferably $T_3$ medium (tryptone 3 g/l, tryptose 2 g/l, yeast extract 1.5 g/l, 5 mg $MnCl_2$, 0.05 M $Na_2HPO_4.2H_2O$, 0.05 M $NaH_2PO_4.H_2O$, pH 6.8 and 1.5% agar), preferably at 28° C. For long term storage, it is preferred to mix an equal volume of a spore-crystal suspension with an equal volume of 50% glycerol and store this at −70° C. or lyophilize a spore-crystal suspension. For sporulation, growth on $T_3$ medium is preferred for 72 hours at 28° C., followed by storage at 4° C. The crystal proteins produced by the strains during sporulation are packaged in crystals.

Example 2

Insecticidal Activity of the BtS02072BG and BtS02739C Strains Against Selected Lepidopteran Insect Species Toxicity assays were performed on neonate larvae of *Helicoverpa zea*, *Heliothis virescens*, *Ostrinia nubilalis*, *Spodoptera frugiperda* and *Sesamia nonagrioides* fed on an artificial diet layered with spore-crystal mixtures from either BtS02072BG or BtS02739C, at about $10^9$ spore-crystals per ml.

The artificial diet (Vanderzant, 1962) was dispensed in wells of Costar 24-well plates for tests on *H. zea, H. virescens* and *O. nubilalis.* 50 microliter of the spore-crystal mixture was applied on the surface of the diet and dried in a laminar air flow. For tests on *H. zea, H. virescens*, one larva was placed in each well and 20 larvae were used per sample. For tests on *O. nubilalis,* 2 larvae were placed in each well and 24 larvae were used per sample. The artificial diet was dispensed in wells of Costar 48-well plates for tests on *S. frugiperda* and *S. nonagrioides.* 25 microliter of the spore-crystal mixture was applied on the surface of the diet and dried in a laminar air flow. One larva was placed in each well and 18 larvae were used per sample. Dead and living larvae were counted on the seventh day. The percentage of dead larvae are shown in Table I below.

TABLE I

| Percentage of dead larvae upon application of crystal-spore mixture to insects: | | |
|---|---|---|
| | BTS02072BG | BTS02739C |
| *H. zea* | 70 | 15 |
| *H. virescens* | 85-50 | 80-60 |
| *O. nubilalis* | 92 | 72 |
| *S. frugiperda* | 6 | Not tested |
| *S. nonagroides* | 100 | Not tested |

Example 3

Characterization of New Cry Genes

The BtS02739C genes were detected by PCR using degenerate primers targeting conserved regions in known cry genes. The resulting amplification product was purified using the Wizard PCR preps (Promega) purification system and ligated into pGEM-T vector (Promega). The ligation mixture was electroporated into *E. coli* JM101. A miniprep was made of at least 40 insert-containing transformants, and digests were performed with selected restriction enzymes. Following electrophoresis of the digested miniprep DNA, different DNA fragment patterns could be observed. For each pattern at least one colony was selected. An appropriate DNA prep was made in order to determine the sequence of the insert of the plasmid present in each selected colony. Alignment of the determined sequences of the amplification products with publicly available cry sequences demonstrates that strain BtS02739C contains a novel cry1J-type gene and a novel cry9-type gene.

The BtS02072BG gene was detected as follow. First, a PCR was performed using degenerate crystal protein gene primers on strain BtS02419J. The resulting amplification product was used as template in a secondary PCR using degenerate crystal protein primers The resulting amplification product was purified using the Wizard PCR preps (Promega) purification system and ligated into pGEM-T vector (Promega). The ligation mixture was electroporated into XL1 Blue *E. coli*. A miniprep was made of at least 40 insert-containing transformants, and digests were performed with selected restriction enzymes. Following electrophoresis of the digested miniprep DNA, different DNA fragment patterns could be observed. For each pattern at least one colony was selected. An appropriate DNA prep was made in order to determine the sequence of the insert of the plasmid present in each selected colony.

From the cloned amplification products from strain BtS02419J, a sequence was found to be identical to the corresponding fragment of cry1Be1, except for one nucleotide difference. Next, primers were selected to evaluate the presence of a cry sequence similar to that of the sequenced cry gene fragment from BtS02419J in a number of Bt strains, one of them being strain BtS02072BG. These primers had the following sequence (5' to 3'):

```
Forward primer: cry1B.fw:
CAG TCC AAA CGG GTA TAA AC

Reverse primer: B.R:
CTG CTT CGA AGG TTG CAG TA
```

Alignment of the determined sequences from the amplification products with publicly available cry sequences demonstrates that strain BtS02072BG contains a novel cry1B-type gene.

Example 4

Cloning and Expression of the Cry Genes

In order to isolate the full length cry1J-type and cry9-type gene from BtS02739C, and the cry1B-type gene from BtS02072BG, total DNA from these strains was prepared and partially digested with Sau3A. The digested DNA was size fractionated on a sucrose gradient and fragments ranging from 5 Kb to 10 Kb were ligated to the BamH1-digested and TsAP (thermosensitive alkaline phosphatase)-treated cloning vector pUC19 (Yannisch-Perron et al, 1985). The ligation mixture was electroporated in *E. coli* XL1-Blue or *E. coli* JM109 cells. Transformants were plated on LB-triacillin plates containing Xgal and IPTG and white colonies were selected to be used in filter hybridization experiments. Recombinant *E. coli* clones containing the vector were then screened with the appropriate DIG labeled probes. These probes were prepared as follows. First, a PCR was performed using as template cells from a recombinant *E. coli* clone containing a plasmid harboring the particular cry gene fragment, previously amplified using appropriate primers as shown in Table II.

TABLE II primers used to isolate novel Bt DNA sequences (Y = C or T, S = G or C):

| strain | gene | primer | Length of amplified fragment | Primer sequence |
|---|---|---|---|---|
| 2739C | cry1J-type | JFW | 365 bp | GCA GCT AAT GCT ACC ACA TC |
| | | JRV | | GTG GCG GTA TGC TGA CTA AT |
| | cry9-type | 9FW | 576 | GYT TTT ATT CGC CCG CCA CA |
| | | 9RV | | CGA CAG TAG SAC CCA CTA CT |
| 2072BG | cry1B-type | B.F | 922 | CAG CGT ATT AAG TCG ATG GA |
| | | B.R | | CTG CTT CGA AGC TTG CAG TA |

The resulting amplification product was gel-purified and used as template in a secondary PCR reaction using DIG-labeled dNTPs. An appropriate amount of this amplification product was used in hybridization reactions.

Colony hybridization for strain BtS02739C was performed with a mixture of the cry1J-type probe and the cry9-type probe. Positive colonies were then hybridized with each probe separately. Colony hybridization for strain BtS02072BG was performed with the cry1B-type probe. Following identification of a positive colony containing a plasmid harboring the full length cry gene, the sequence of the cry gene was determined using the dye terminator labeling method and a Perkin Elmer ABI Prism-377 DNA sequencer for both strands. Upon DNA sequencing, the genes were termed as follows: the cry1J-type and cry9-type gene from BtS02739C were named cry1Jd and cry9Fa, respectively, and the cry1B-type gene from BtS02072BG was named cry1Bf. The genomic sequences of the isolated cry1Jd, cry9Fa, and cry1Bf genes, as well as the proteins they encode, are shown in the Sequence Listing included in this application. Comparison of the sequences with known Cry DNA or protein sequences showed that the sequences are novel and differ in a substantial number of nucleotides or amino acids from known Bt genes and proteins. Tables III-V provide an overview of the sequence identity with respect to the coding regions of the most similar genes and proteins (both protoxin as toxin forms) as determined using the GAP program of the Wisconsin package of GCG (Madison, Wis., USA) version 10.0. GCG defaults were used within the GAP program. For nucleic acid sequence comparisons, the nwsgapdna scoring matrix was used, for amino acid sequence comparisons, the blosum62 scoring matrix. The toxin form, as used in Tables III-V, refers to the protein starting at the first amino acid and ending two amino acids beyond the last amino acid (usually a proline) of conserved sequence block 5, as defined in Schnepf et al. (1998). The protoxin form refers to the entire protein or coding region of the Bt protein/gene.

TABLE III

Sequence identities for cry1Bf/Cry1Bf:

| DNA | cry1Ba1 | cry1Bb1 | cry1Bc1 | cry1Bd1 | cry1Be1 |
|---|---|---|---|---|---|
| Protoxin | 91.912 | 83.890 | 77.207 | 83.565 | 93.774 |
| Toxin | 86.562 | 74.922 | 74.922 | 75.342 | 89.220 |

TABLE III-continued

Sequence identities for cry1Bf/Cry1Bf:

| Protein | Cry1Ba1 | Cry1Bb1 | Cry1Bc1 | Cry1Bd1 | Cry1Be1 |
|---|---|---|---|---|---|
| Protoxin | 89.869 | 80.193 | 75.795 | 80.933 | 92.170 |
| Toxin | 82.520 | 67.868 | 67.868 | 70.142 | 86.499 |

TABLE IV

Sequence identities for cry9Fa/Cry9Fa:

| DNA | cry9Aa1 | cry9Ba1 | cry9Ca1 | cry9Da1 | cry9Ea1 |
|---|---|---|---|---|---|
| Protoxin | 71.592 | 78.212 | 76.614 | 81.197 | 84.043 |
| Toxin | 51.782 | 62.720 | 68.215 | 75.593 | 81.618 |
| Protein | Cry9Aa1 | Cry9Ba1 | Cry9Ca1 | Cry9Da1 | Cry9Ea1 |
| Protoxin | 62.445 | 72.064 | 71.553 | 76.963 | 82.578 |
| Toxin | 35.828 | 52.167 | 59.133 | 68.372 | 78.858 |

TABLE V

Sequence identities for cry1Jd/Cry1Jd:

| DNA | cry1Ja1 | cry1Jb1 | cry1Jc1 |
|---|---|---|---|
| protoxin | 83.233 | 83.176 | 86.323 |
| toxin | 79.526 | 81.162 | 88.143 |
| protein | Cry1Ja1 | Cry1Jb1 | Cry1Jc1 |
| protoxin | 79.759 | 78.830 | 82.489 |
| toxin | 71.574 | 74.746 | 81.711 |

Genomic clones of the newly isolated genes have been deposited at the BCCM™-LMBP (Belgian Coordinated Collections of Microorganisms—Laboratorium voor Moleculaire Biologie-Plasmidencollectie, University of Gent, K.L. Ledeganckstraat 35, B-9000 Gent, Belgium) under the following accession numbers:

LMBP 3983 for *E coli* JM109 containing plasmid pUC2739C/1Jd1 comprising the cry1Jd gene, deposited on Nov. 25, 1999 (this gene can be isolated from this plasmid on an about 8.4 kb DNA fragment by digestion with XhoI and SmaI);

LMBP 3984 for *E coli*JM109 containing plasmid pUC2739C/9Fa1 comprising the cry9Fa gene, deposited on Nov. 25, 1999 (this gene can be isolated from this plasmid on an about 8 kb DNA fragment by digestion with SacI and PstI); and LMBP 3986 for *E coli* XL1 Blue containing plasmid pUC2072BG/1 Bf1 comprising the cry1Bf gene, deposited on Nov. 25, 1999 (this gene can be isolated from this plasmid on an about 7 kb DNA fragment by digestion with SacI and SalI).

Example 5

Insecticidal Activity of the Cry Genes

The insert containing the cry9Fa gene was subcloned into a suitable shuttle vector and the resulting plasmid pSL2739C/9Fa1 was introduced by routine procedures into a crystal-minus Bt strain. The crystal protein produced by a sporulated culture of this recombinant Bt strain was tested on neonate larvae of *H. virescens* and *O. nubilalis* at a concentration of about $10^9$ particles/ml. On *O. nubilalis* larvae, 100% mortality was observed, whereas 72% mortality was observed on *H. virescens* larvae, whereas after treatment with the crystal-minus control strain all larvae survived.

The insert containing the cry1Bf gene was subcloned into a suitable shuttle vector and the resulting plasmid pSL2072BG/1Bf was introduced by routine procedures into a crystal-minus Bt strain. The crystal protein produced by a sporulated culture of this recombinant Bt strain was tested on larvae of *Sesamia nonagrioides, Heliothis virescens, Helicoverpa zea* and *O. nubilalis* at different concentrations. Significant high mortality of the Cry1Bf toxin was observed on *H. virescens, Ostrinia nubilialis* and *Sesamia nonagrioides*, while lower toxicity was found on *Helicoverpa zea*. After treatment with the crystal-minus control strain all larvae survived.

The insert containing the cry1Jd gene was subcloned into a suitable shuttle vector and the resulting plasmid pGI2739C/1Jd was introduced by routine procedures into a crystal-minus Bt strain. The crystal protein produced by a sporulated culture of this recombinant Bt strain is tested on larvae of *Heliothis virescens* at different concentrations, and significant mortality of the Cry1Jd toxin was observed. After treatment with the crystal-minus control strain all larvae survived.

Example 6

Production of the Novel Cry Proteins in Transformed Plants

Chimeric genes encoding the truncated forms of the Cry1Bf, Cry1Jd, and Cry9Fa proteins are made as described in EP 0 193 259 and published PCT patent application WO 94/12264, using the CaMV 35S (Hull and Howell, 1987) and ubiquitin (Christensen et al., 1992) promoters. Preferably, the codon usage of the open reading frame is adapted to that of the host plant so as to optimize expression efficiency, as described in published PCT patent application WO 94/12264.

Rice, cotton and corn cells are transformed with the resulting chimeric genes. Corn cells are stably transformed by either *Agrobacterium*-mediated transformation (Ishida et al., 1996, and U.S. Pat. No. 5,591,616) or by electroporation using wounded and enzyme-degraded embryogenic callus, as described in WO 92/09696 or U.S. Pat. No. 5,641,664 (incorporated herein by reference).

Cotton cells are stably transformed by *Agrobacterium*-mediated transformation (Umbeck et al., 1987, Bio/Technology 5, 263-266; U.S. Pat. No. 5,004,863, incorporated herein by reference). Rice cells are stably transformed with the method described in published PCT patent application WO 92/09696.

Regenerated transformed corn, cotton and rice plants are selected by ELISA, Northern and Southern blot and insecticidal effect. Chimeric gene-containing progeny plants show improved resistance to insects compared to untransformed control plants with appropriate segregation of insect resistance and the transformed phenotype. Protein and RNA measurements show that increased insect resistance is linked with higher expression of the novel Cry protein in the plants.

References Cited

Adang et al. (1985). Gene 36, 289.
Bennetzen & Hall. (1982). J. Biol. Chem. 257, 3026-3031.
Berhard, K. and Utz, R., "Production of *Bacillus thuringiensis* insecticides for experimental and commercial uses", In *Bacillus thuringiensis*, An Environmental Biopesticide: Theory and Practice, pp. 255-267, eds. Entwistle, P. F., Cory, J. S., Bailey, M. J. and Higgs, S., John Wiley and Sons, New York (1993).
Christensen et al. (1992) Plant mol. Biol. 18, 675-689.
Cornejo et al. (1993) Plant Mol. Biol. 23, 567-581.
Crickmore et al. (1998) Microbiol. Mol. Biol. Rev. 62(3), 807-13.
Datta S., Peterhans A., Datta K. and Potrykus I., Bio/Technology 8, 736-740 (1990).
Dulmage, H. T., "Production of Bacteria for Biological Control of Insects" in Biological Control in Crop Production, Ed. Paparizas, D.C., Osmun Publishers, Totowa, N.J., USA, pp. 129-141 (1981).
Finney, Probit Analysis, 3rd Edition, Cambridge University Press (1971)
Franck, Guilley, Jonard, Richards and Hirth, Cell 21, 285-294 (1980)
French, B. T., Maul, H. N. and Maul, G. G., Anal. Biochem. 156, 417-423 (1986)
Fromm M., Morrish F., Armstrong C., Williams R., Thomas J. and Klein T., Bio/Technology 8, 833-839 (1990).
Gardner, Howarth, Hahn, Brown-Luedi, Shepard and Messing, Nucleic Acids Research 9, 2871-2887 (1981)
Ge A., Rivers D., Milne R. and Dean D., J. Biol. Chem. 266, 17954-17958 (1991)
Gielen, J., De Beukeleer, M., Seurinck, J., Deboeck, F., De Greve, H., Lemmers, M., Van Montagu, M. and Schell, J., EMBO J. 3, 835-845 (1984).
Gordon-Kamm W., Spencer M., Mangano M., Adams T., Daines R., Start W., O'Brien J., Chambers S., Adams W., Willets N., Rice T., Mackey C., Krueger R., Kausch A. and Lemaux P., The Plant Cell 2, 603-618 (1990).
Gould, J., Devey, M., Hasegawa, O., Ulian, E. C., Peterson, G. and Smith, R. H., Plant Physiol. 95, 426-434 (1991).
Ho et al. (1989). Gene 77, 51-59.
Höfte, H., Van Rie, J., Jansens, S., Van Houtven, A., Verbruggen, H. and Vaeck, M., Applied and Environmental Microbiology 54, 2010-2017 (1988)
Höfte H. and Whiteley H. R., Microbiological Review 53, 242-255 (1989).
Hull and Howell, Virology 86, 482-493 (1987)
Ishida et al., 1996, Nature Biotechnology 14, 745-750.
Itakura et al. (1977). Science 198, 1056-1063.
Jansens et al. (1997) Crop Science 37, 1616-1624.
Last et al. (1990) Theor. Appl. Genet. 81, 581-888.
Lereclus, D.; Vallade, M.; Chaufaux, J.; Arantes, O. & Rambaud, S., Bio/Technology 10, 418 (1992).
Mahillon et al, FEMS Microbiol. Letters 60, 205-210 (1989).
Maxam, A. M. and Gilbert, W., Methods in Enzymol. 65, 499-560 (1980).
McBride et al., 1995, Bio/Technology 13, 362
Murray, E., Lotzer, J. and Eberle, M., Nucleic Acids Research 17(2), 477-498 (1989).
Sanger et al., Proc. Natl. Acad. Sci. USA. 74(12), 5463-5467 (1977).
Schnepf et al. (1985). Journal of Biological Chemistry 260, 6264.
Schnepf et al. (1998). Microbiol. Mol. Biol. Rev. 62(3), 775-806.
Shimamoto K., Terada R., Izawa T. and Fujimoto H., Nature 338, 274-276 (1989).
Stanssens P., Opsomer C., McKeown Y., Kramer W., Zabeau M. and Fritz H. J., Nucleic Acids Research 12, 4441-4454 (1989).
Vaeck, M., Reynaerts, A., Höfte, H., Jansens, S., De Beuckeleer, M., Dean, C., Zabeau, M.,
Vanderzant, J. Econ. Entomol. 55, p. 140 (1962).
Van Montagu, M. and Leemans, J., Nature 327, 33-37 (1987).
Van Rie et al., Science 247, 72 (1990).

Velten, J., Velten, L., Hain, R. and Schell, J., EMBO J. 3, 2723-2730 (1984).

Velten, J. and Schell, J. Nucleic Acids Research 13, 6981-6998 (1985)

Visser, B., Bosch, D. and Honée, G., "Domain-Structure Studies of *Bacillus thuringiensis* Crystal Proteins: A Genetic Approach", In *Bacillus thuringiensis*, An Environmental Biopesticide: Theory and Practice, pp. 71-88, eds. Entwistle, P. F., Cory, J. S., Bailey, M. J. and Higgs, S., John Wiley and Sons, New York (1993).

Wada et al. (1990). Nucl. Acids Res. 18, 2367-1411.

White et al. (1989). Trends in Genet. 5, 185-189.

Yannisch-Perron, C., Vierra, J. and Messing, J., Gene 33, 103-119 (1985).

Zhang et al. (1991) The Plant Cell 3, 1155-1165.

The invention claimed is:

1. An recombinant DNA encoding an insecticidal protein, comprising an amino acid sequence with at least 95% sequence identity to the amino acid sequence of SEQ ID No. 4 from amino acid position 1 to amino acid position 596.

2. The DNA of claim 1, encoding a protein comprising the amino acid sequence of SEQ ID No. 4 from amino acid position 1 to amino acid position 596.

3. The DNA of claim 2, encoding a protein comprising the amino acid sequence of SEQ ID No. 4.

4. The DNA of claim 1, wherein said DNA hybridizes under stringent hybridization conditions to the DNA of SEQ ID No. 3, wherein said stringent hybridization is by:
   a) immobilizing DNA on a filter, and prehybridizing said filter for 1 to 2 hours in prehybridization fluid comprised of either 50% formamide, 5% SSPE, 2×Denhardt's reagent and 0.1% SDS at 42 ° C., or 6×SSC, 2×Denhardt's reagent and 0.1% SDS at 68 ° C.;
   b) adding a denatured labeled probe comprising DNA of SEQ ID No. 3 directly to the prehybridization fluid and incubating for 16 to 24 hours at 42 ° C. if that was the temperature used in step a), or at 68 ° C. if that was the temperatuve used in step a);
   c) after incubation, washing the filters for 20 minutes at room temperature in 1×SSC, 0.1% SDS, followed by three washes of 20 minutes each at 68 ° C. in 0.2 ×SSC and 0.1% SDS;
   d) establishing an autoradiograph by exposing the filters for 24 to 48 hours to X-ray film at −70 ° C. with an intensifying screen.

5. The DNA of claim 1, comprising an artificial DNA sequence having a different codon usage compared to the DNA sequence of SEQ ID NO: 3.

6. A chimeric gene comprising the DNA of claim 1, operably-linked to a plant-expressible promoter.

7. A plant cell, plant or seed transformed to contain the chimeric gene of claim 6.

8. The plant cell, plant or seed of claim 7, comprising said chimeric gene integrated in the nuclear or chloroplast DNA of their cells.

9. The plant cell, plant or seed of claim 8, which is selected from the group consisting of: corn, cotton, rice, oilseed rape, *Brassica* species, eggplant, soybean, potato, sunflower, tomato, sugarcane, tea, beans, tobacco, strawberry, clover, cucumber, watermelon, pepper, oat, barley, wheat, dahlia, gladiolus, chrysanthemum, sugarbeet, sorghum, alfalfa, and peanut cells, plants or seeds.

10. A micro-organism, transformed to contain the DNA of claim 1.

11. The micro-organism of claim 10, which is selected from the genus *Agrobacterium, Escherichia*, or *Bacillus*.

12. A process for controlling insects, said process comprising expressing the DNA of claim 1, or a chimeric gene comprising said DNA operably-linked to a plant-expressible promoter, in host cells, and contacting insects with said host cells.

13. A process for obtaining a plant with resistance to insects, said process comprising transforming plant cells with the DNA of claim 1, or with a chimeric gene comprising said DNA operably-linked to a plant-expressible promoter, and regenerating transformed plants and progeny thereof which are resistant to insects.

14. The process of claim 12, wherein said insects are larvae of *Heliothis virescens*.

15. The process of claim 13, wherein said insects are larvae of *Heliothis virescens*.

16. The process of claim 13, further comprising obtaining seed from said plants comprising said DNA.

* * * * *

SEQUENCE LISTING

```
<160> NUMBER OF SEQ ID NOS: 13

<210> SEQ ID NO 1
<211> LENGTH: 3687
<212> TYPE: DNA
<213> ORGANISM: Bacillus thuringiensis
<220> FEATURE:
<221> NAME/KEY: CDS
<222> LOCATION: (1)..(3687)

<400> SEQUENCE: 1 ttg act tca aat agg aaa aat gag aat gaa att ata aat gct tta tcg       48
Leu Thr Ser Asn Arg Lys Asn Glu Asn Glu Ile Ile Asn Ala Leu Ser
  1               5                  10                  15 att cca gct gta tcg aat cat tcc aca caa atg gat cta tca cca gat       96
Ile Pro Ala Val Ser Asn His Ser Thr Gln Met Asp Leu Ser Pro Asp
             20                  25                  30 gct cgt att gag gat tct ttg tgt ata gcc gag ggg aat aat atc aat      144
Ala Arg Ile Glu Asp Ser Leu Cys Ile Ala Glu Gly Asn Asn Ile Asn
         35                  40                  45 cca ctt gtt agc gca tca aca gtc caa acg ggt att aac ata gct ggt      192
Pro Leu Val Ser Ala Ser Thr Val Gln Thr Gly Ile Asn Ile Ala Gly
     50                  55                  60 aga ata cta ggt gta tta ggc gta ccg ttt gct gga caa ata gct agt      240
Arg Ile Leu Gly Val Leu Gly Val Pro Phe Ala Gly Gln Ile Ala Ser
 65                  70                  75                  80 ttt tat agt ttt ctt gtt ggt gaa tta tgg ccc cgc ggc aga gat cag      288
Phe Tyr Ser Phe Leu Val Gly Glu Leu Trp Pro Arg Gly Arg Asp Gln
                 85                  90                  95 tgg gaa att ttc cta gaa cat gtc gaa caa ctt ata aat caa caa ata      336
Trp Glu Ile Phe Leu Glu His Val Glu Gln Leu Ile Asn Gln Gln Ile
            100                 105                 110 aca gaa aat gct agg aat acg gca ctt gct cga tta caa ggt tta gga      384
Thr Glu Asn Ala Arg Asn Thr Ala Leu Ala Arg Leu Gln Gly Leu Gly
        115                 120                 125 gat tcc ttt aga gcc tat caa cag tca ctt gaa gat tgg cta gaa aac      432
Asp Ser Phe Arg Ala Tyr Gln Gln Ser Leu Glu Asp Trp Leu Glu Asn
    130                 135                 140 cgt gat gat gca aga acg aga agt gtt ctt tat acc caa tat ata gcc      480
Arg Asp Asp Ala Arg Thr Arg Ser Val Leu Tyr Thr Gln Tyr Ile Ala
145                 150                 155                 160 tta gaa ctt gat ttt ctt aat gcg atg ccg ctt ttc gca att aga aac      528
Leu Glu Leu Asp Phe Leu Asn Ala Met Pro Leu Phe Ala Ile Arg Asn
                165                 170                 175 caa gaa gtt cca tta tta atg gta tat gct caa gct gca aat tta cac      576
Gln Glu Val Pro Leu Leu Met Val Tyr Ala Gln Ala Ala Asn Leu His
            180                 185                 190 cta tta tta ttg aga gat gcc tct ctt ttt ggt agt gaa ttt ggg ctt      624
Leu Leu Leu Leu Arg Asp Ala Ser Leu Phe Gly Ser Glu Phe Gly Leu
        195                 200                 205 aca tcg cag gaa att caa cgt tat tat gag cgc caa gtg gaa caa acg      672
Thr Ser Gln Glu Ile Gln Arg Tyr Tyr Glu Arg Gln Val Glu Gln Thr
```

```
                  210                 215                 220
aga gat tat tcc gac tat tgc gta gaa tgg tat aat aca ggt cta aat       720
Arg Asp Tyr Ser Asp Tyr Cys Val Glu Trp Tyr Asn Thr Gly Leu Asn
225                 230                 235                 240 agc ttg aga ggg aca aat gcc gca agt tgg gtg cgt tat aat caa ttc       768
Ser Leu Arg Gly Thr Asn Ala Ala Ser Trp Val Arg Tyr Asn Gln Phe
                245                 250                 255 cgt aga gat cta acg tta ggg gta tta gat cta gtg gca cta ttc cca       816
Arg Arg Asp Leu Thr Leu Gly Val Leu Asp Leu Val Ala Leu Phe Pro
        260                 265                 270 agc tat gac act cgc act tat cca ata aat acg agt gct cag tta aca       864
Ser Tyr Asp Thr Arg Thr Tyr Pro Ile Asn Thr Ser Ala Gln Leu Thr
    275                 280                 285 agg gaa gtt tat aca gac gca att gga gca aca ggg gta aat atg gca       912
Arg Glu Val Tyr Thr Asp Ala Ile Gly Ala Thr Gly Val Asn Met Ala
290                 295                 300 agt atg aat tgg tat aat aat aat gca cct tcg ttt tcc gct ata gag       960
Ser Met Asn Trp Tyr Asn Asn Asn Ala Pro Ser Phe Ser Ala Ile Glu
305                 310                 315                 320 act gcg gtt atc cga agc ccg cat cta ctt gat ttt cta gaa caa ctt      1008
Thr Ala Val Ile Arg Ser Pro His Leu Leu Asp Phe Leu Glu Gln Leu
                325                 330                 335 aca att ttt agc act tca tca cga tgg agt gct act agg cat atg act      1056
Thr Ile Phe Ser Thr Ser Ser Arg Trp Ser Ala Thr Arg His Met Thr
        340                 345                 350 tac tgg cgg ggg cac aca att caa tct cgg cca ata gga ggc gga tta      1104
Tyr Trp Arg Gly His Thr Ile Gln Ser Arg Pro Ile Gly Gly Gly Leu
    355                 360                 365 aat acc tca acg cat ggg tct acc aat act tct att aat cct gta aga      1152
Asn Thr Ser Thr His Gly Ser Thr Asn Thr Ser Ile Asn Pro Val Arg
370                 375                 380 tta tca ttc ttc tct cga gac gta tat tgg act gaa tca tat gca gga      1200
Leu Ser Phe Phe Ser Arg Asp Val Tyr Trp Thr Glu Ser Tyr Ala Gly
385                 390                 395                 400 gtg ctt cta tgg gga att tac ctt gaa cct att cat ggt gtc cct act      1248
Val Leu Leu Trp Gly Ile Tyr Leu Glu Pro Ile His Gly Val Pro Thr
                405                 410                 415 gtt aga ttt aat ttt agg aac cct cag aat act ttt gaa aga ggt act      1296
Val Arg Phe Asn Phe Arg Asn Pro Gln Asn Thr Phe Glu Arg Gly Thr
        420                 425                 430 gct aac tat agt caa ccc tat gag tca cct ggg ctt caa tta aaa gat      1344
Ala Asn Tyr Ser Gln Pro Tyr Glu Ser Pro Gly Leu Gln Leu Lys Asp
    435                 440                 445 tca gaa act gaa tta cca cca gaa aca aca gaa cga cca aat tat gaa      1392
Ser Glu Thr Glu Leu Pro Pro Glu Thr Thr Glu Arg Pro Asn Tyr Glu
450                 455                 460 tca tat agt cat agg tta tct cac ata ggg ctc att tca caa tct agg      1440
Ser Tyr Ser His Arg Leu Ser His Ile Gly Leu Ile Ser Gln Ser Arg
465                 470                 475                 480 gtg cat gta cca gta tat tct tgg acg cac cgt agt gca gat cgt aca      1488
Val His Val Pro Val Tyr Ser Trp Thr His Arg Ser Ala Asp Arg Thr
                485                 490                 495 aat acc att agt tca gat agc ata aca caa ata cca ttg gta aaa tca      1536
Asn Thr Ile Ser Ser Asp Ser Ile Thr Gln Ile Pro Leu Val Lys Ser
        500                 505                 510 ttc aac ctt aat tca ggt acc tct gta gtc agt ggc cca gga ttt aca      1584
Phe Asn Leu Asn Ser Gly Thr Ser Val Val Ser Gly Pro Gly Phe Thr
    515                 520                 525 gga ggg gat ata atc cga act aac gtt aat ggt agt gta cta agt atg      1632
Gly Gly Asp Ile Ile Arg Thr Asn Val Asn Gly Ser Val Leu Ser Met
```

-continued

|  |  |  |  |  |
|---|---|---|---|---|
| 530 | | 535 | | 540 |

```
ggt ctt aat ttt aat aat aca tca tta cag cgg tat cgc gtg aga gtt    1680
Gly Leu Asn Phe Asn Asn Thr Ser Leu Gln Arg Tyr Arg Val Arg Val
545                 550                 555                 560 cgt tat gct gct tct caa aca atg gtc ctg agg gta act gtc gga ggg    1728
Arg Tyr Ala Ala Ser Gln Thr Met Val Leu Arg Val Thr Val Gly Gly
                565                 570                 575 agt act act ttt gat caa gga ttc cct agt act atg agt gca aat gag    1776
Ser Thr Thr Phe Asp Gln Gly Phe Pro Ser Thr Met Ser Ala Asn Glu
            580                 585                 590 tct ttg aca tct caa tca ttt aga ttt gca gaa ttt cct gta ggt att    1824
Ser Leu Thr Ser Gln Ser Phe Arg Phe Ala Glu Phe Pro Val Gly Ile
        595                 600                 605 agt gca tct ggc agt caa act gct gga ata agt ata agt aat aat gca    1872
Ser Ala Ser Gly Ser Gln Thr Ala Gly Ile Ser Ile Ser Asn Asn Ala
    610                 615                 620 ggt aga caa acg ttt cac ttt gat aaa att gaa ttc att cca att act    1920
Gly Arg Gln Thr Phe His Phe Asp Lys Ile Glu Phe Ile Pro Ile Thr
625                 630                 635                 640 gca acc ttc gaa gca gaa tac gat tta gaa agg gcg caa gag gcg gtg    1968
Ala Thr Phe Glu Ala Glu Tyr Asp Leu Glu Arg Ala Gln Glu Ala Val
                645                 650                 655 aat gct ctg ttt act aat acg aat cca aga aga ttg aaa aca gat gtg    2016
Asn Ala Leu Phe Thr Asn Thr Asn Pro Arg Arg Leu Lys Thr Asp Val
            660                 665                 670 aca gat tat cat att gat caa gta tcc aat tta gtg gcg tgt tta tcg    2064
Thr Asp Tyr His Ile Asp Gln Val Ser Asn Leu Val Ala Cys Leu Ser
        675                 680                 685 gat gaa ttc tgc tta gat gaa aag aga gaa tta ctt gag aaa gtg aaa    2112
Asp Glu Phe Cys Leu Asp Glu Lys Arg Glu Leu Leu Glu Lys Val Lys
    690                 695                 700 tat gcg aaa cga ctc agt gat gaa aga aac tta ctc caa gat cca aac    2160
Tyr Ala Lys Arg Leu Ser Asp Glu Arg Asn Leu Leu Gln Asp Pro Asn
705                 710                 715                 720 ttc aca tcc atc aat aag caa cca gac ttc ata tct act aat gag caa    2208
Phe Thr Ser Ile Asn Lys Gln Pro Asp Phe Ile Ser Thr Asn Glu Gln
                725                 730                 735 tcg aat ttc aca tct atc cat gaa caa tct gaa cat gga tgg tgg gga    2256
Ser Asn Phe Thr Ser Ile His Glu Gln Ser Glu His Gly Trp Trp Gly
            740                 745                 750 agt gag aac att aca atc cag gaa gga aat gac gta ttt aaa gag aat    2304
Ser Glu Asn Ile Thr Ile Gln Glu Gly Asn Asp Val Phe Lys Glu Asn
        755                 760                 765 tac gtc aca cta ccg ggg act ttt aat gag tgt tat ccg acg tat tta    2352
Tyr Val Thr Leu Pro Gly Thr Phe Asn Glu Cys Tyr Pro Thr Tyr Leu
    770                 775                 780 tat caa aaa ata gga gag tcg gaa tta aaa gct tat act cgc tac caa    2400
Tyr Gln Lys Ile Gly Glu Ser Glu Leu Lys Ala Tyr Thr Arg Tyr Gln
785                 790                 795                 800 tta aga ggg tat att gaa gat agt caa gat tta gag ata tat ttg att    2448
Leu Arg Gly Tyr Ile Glu Asp Ser Gln Asp Leu Glu Ile Tyr Leu Ile
                805                 810                 815 cgt tat aat gcg aaa cat gaa aca ttg gat gtt cca ggt acc gag tcc    2496
Arg Tyr Asn Ala Lys His Glu Thr Leu Asp Val Pro Gly Thr Glu Ser
            820                 825                 830 gta tgg ccg ctt tca gtt gaa agc cca atc gga agg tgc gga gaa ccg    2544
Val Trp Pro Leu Ser Val Glu Ser Pro Ile Gly Arg Cys Gly Glu Pro
        835                 840                 845 aat cga tgc gca cca cat ttt gaa tgg aat cct gat cta gat tgt tcc    2592
Asn Arg Cys Ala Pro His Phe Glu Trp Asn Pro Asp Leu Asp Cys Ser
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 850 |     |     |     |     | 855 |     |     |     |     | 860 |     |     |      |
| tgc | aga | gat | gga | gaa | aaa | tgt | gcg | cat | cat | tcc | cat | cat | ttc | tct | ttg | 2640 |
| Cys | Arg | Asp | Gly | Glu | Lys | Cys | Ala | His | His | Ser | His | His | Phe | Ser | Leu |      |
| 865 |     |     |     |     | 870 |     |     |     |     | 875 |     |     |     |     | 880 |      |
| gat | att | gat | att | gga | tgc | aca | gac | ttg | cat | gag | aat | cta | ggc | gtg | tgg | 2688 |
| Asp | Ile | Asp | Ile | Gly | Cys | Thr | Asp | Leu | His | Glu | Asn | Leu | Gly | Val | Trp |      |
|     |     |     |     | 885 |     |     |     |     | 890 |     |     |     |     | 895 |     |      |
| gtg | gta | ttc | aag | att | aag | acg | cag | gaa | ggt | cat | gca | aga | cta | ggg | aat | 2736 |
| Val | Val | Phe | Lys | Ile | Lys | Thr | Gln | Glu | Gly | His | Ala | Arg | Leu | Gly | Asn |      |
|     |     |     | 900 |     |     |     |     | 905 |     |     |     |     | 910 |     |     |      |
| ctg | gaa | ttt | att | gaa | gag | aaa | cca | tta | tta | gga | gaa | gca | ctg | tct | cgt | 2784 |
| Leu | Glu | Phe | Ile | Glu | Glu | Lys | Pro | Leu | Leu | Gly | Glu | Ala | Leu | Ser | Arg |      |
|     |     | 915 |     |     |     |     | 920 |     |     |     |     | 925 |     |     |     |      |
| gtg | aag | aga | gca | gag | aaa | aaa | tgg | aga | gac | aaa | cgt | gaa | aaa | cta | caa | 2832 |
| Val | Lys | Arg | Ala | Glu | Lys | Lys | Trp | Arg | Asp | Lys | Arg | Glu | Lys | Leu | Gln |      |
|     | 930 |     |     |     |     | 935 |     |     |     |     | 940 |     |     |     |     |      |
| ttg | gaa | aca | aaa | cga | gta | tat | aca | gag | gca | aaa | gaa | gct | gtg | gat | gct | 2880 |
| Leu | Glu | Thr | Lys | Arg | Val | Tyr | Thr | Glu | Ala | Lys | Glu | Ala | Val | Asp | Ala |      |
| 945 |     |     |     |     | 950 |     |     |     |     | 955 |     |     |     |     | 960 |      |
| tta | ttt | gta | gat | tct | caa | tat | aat | aga | tta | caa | gcg | gat | aca | aac | att | 2928 |
| Leu | Phe | Val | Asp | Ser | Gln | Tyr | Asn | Arg | Leu | Gln | Ala | Asp | Thr | Asn | Ile |      |
|     |     |     |     | 965 |     |     |     |     | 970 |     |     |     |     | 975 |     |      |
| ggc | atg | att | cat | gcg | gca | gat | aaa | ctt | gtt | cat | cga | att | cga | gag | gct | 2976 |
| Gly | Met | Ile | His | Ala | Ala | Asp | Lys | Leu | Val | His | Arg | Ile | Arg | Glu | Ala |      |
|     |     |     | 980 |     |     |     |     | 985 |     |     |     |     | 990 |     |     |      |
| tat | ctg | tca | gaa | tta | tct | gtt | atc | ccg | ggt | gta | aat | gcg | gaa | att | ttt | 3024 |
| Tyr | Leu | Ser | Glu | Leu | Ser | Val | Ile | Pro | Gly | Val | Asn | Ala | Glu | Ile | Phe |      |
|     |     | 995 |     |     |     |     | 1000 |    |     |     |     | 1005 |    |     |     |      |
| gaa | gaa | tta | gaa | ggt | cgc | att | atc | act | gca | atc | tcc | cta | tac | gat | gcg | 3072 |
| Glu | Glu | Leu | Glu | Gly | Arg | Ile | Ile | Thr | Ala | Ile | Ser | Leu | Tyr | Asp | Ala |      |
|     | 1010|     |     |     |     | 1015|     |     |     |     | 1020|     |     |     |     |      |
| aga | aat | gtc | gtt | aaa | aat | ggt | gat | ttt | aat | aat | gga | tta | gca | tgc | tgg | 3120 |
| Arg | Asn | Val | Val | Lys | Asn | Gly | Asp | Phe | Asn | Asn | Gly | Leu | Ala | Cys | Trp |      |
| 1025|     |     |     |     | 1030|     |     |     |     | 1035|     |     |     |     | 1040|      |
| aat | gta | aaa | ggg | cat | gta | gat | gta | caa | cag | agc | cat | cac | cgt | tct | gtc | 3168 |
| Asn | Val | Lys | Gly | His | Val | Asp | Val | Gln | Gln | Ser | His | His | Arg | Ser | Val |      |
|     |     |     |     | 1045|     |     |     |     | 1050|     |     |     |     | 1055|     |      |
| ctt | gtt | atc | cca | gaa | tgg | gaa | gca | gaa | gtg | tca | caa | gca | gtt | cgc | gtc | 3216 |
| Leu | Val | Ile | Pro | Glu | Trp | Glu | Ala | Glu | Val | Ser | Gln | Ala | Val | Arg | Val |      |
|     |     |     | 1060|     |     |     |     | 1065|     |     |     |     | 1070|     |     |      |
| tgt | ccg | ggg | cgt | ggc | tat | atc | ctc | cgt | gtc | aca | gcg | tac | aaa | gag | gga | 3264 |
| Cys | Pro | Gly | Arg | Gly | Tyr | Ile | Leu | Arg | Val | Thr | Ala | Tyr | Lys | Glu | Gly |      |
|     |     | 1075|     |     |     |     | 1080|     |     |     |     | 1085|     |     |     |      |
| tat | gga | gag | ggt | tgt | gta | acg | atc | cat | gaa | atc | gag | aac | aat | aca | gac | 3312 |
| Tyr | Gly | Glu | Gly | Cys | Val | Thr | Ile | His | Glu | Ile | Glu | Asn | Asn | Thr | Asp |      |
|     | 1090|     |     |     |     | 1095|     |     |     |     | 1100|     |     |     |     |      |
| gaa | cta | aaa | ttt | aaa | aac | tgt | gaa | gaa | gag | gaa | gtg | tat | cca | acg | gat | 3360 |
| Glu | Leu | Lys | Phe | Lys | Asn | Cys | Glu | Glu | Glu | Glu | Val | Tyr | Pro | Thr | Asp |      |
| 1105|     |     |     |     | 1110|     |     |     |     | 1115|     |     |     |     | 1120|      |
| aca | gga | acg | tgt | aat | gat | tat | act | gca | cac | caa | ggt | aca | gca | gta | tgt | 3408 |
| Thr | Gly | Thr | Cys | Asn | Asp | Tyr | Thr | Ala | His | Gln | Gly | Thr | Ala | Val | Cys |      |
|     |     |     |     | 1125|     |     |     |     | 1130|     |     |     |     | 1135|     |      |
| aat | tcc | cgt | aat | gct | gga | tat | gag | gat | gca | tat | gaa | gtt | gat | act | aca | 3456 |
| Asn | Ser | Arg | Asn | Ala | Gly | Tyr | Glu | Asp | Ala | Tyr | Glu | Val | Asp | Thr | Thr |      |
|     |     |     | 1140|     |     |     |     | 1145|     |     |     |     | 1150|     |     |      |
| gca | tct | gtt | aat | tac | aaa | ccg | act | tat | gaa | gaa | gaa | acg | tat | aca | gat | 3504 |
| Ala | Ser | Val | Asn | Tyr | Lys | Pro | Thr | Tyr | Glu | Glu | Glu | Thr | Tyr | Thr | Asp |      |
|     |     | 1155|     |     |     |     | 1160|     |     |     |     | 1165|     |     |     |      |
| gta | cga | aga | gat | aat | cat | tgt | gaa | tat | gac | aga | ggg | tat | gtg | aat | tat | 3552 |
| Val | Arg | Arg | Asp | Asn | His | Cys | Glu | Tyr | Asp | Arg | Gly | Tyr | Val | Asn | Tyr |      |

-continued

```
                        1170                     1175                      1180
cca  cca  cta  cca  gct  ggt  tat  atg  aca  aaa  gaa  tta  gaa  tac  ttc  cca     3600
Pro  Pro  Leu  Pro  Ala  Gly  Tyr  Met  Thr  Lys  Glu  Leu  Glu  Tyr  Phe  Pro
1185                     1190                     1195                      1200 gaa  acc  gat  aag  gta  tgg  att  gag  att  gga  gaa  acg  gaa  ggg  aag  ttt     3648
Glu  Thr  Asp  Lys  Val  Trp  Ile  Glu  Ile  Gly  Glu  Thr  Glu  Gly  Lys  Phe
                         1205                     1210                      1215 att  gta  gac  agc  gtg  gaa  tta  ctc  ctt  atg  gag  gaa  tag                    3687
Ile  Val  Asp  Ser  Val  Glu  Leu  Leu  Leu  Met  Glu  Glu
               1220                     1225

<210> SEQ ID NO 2
<211> LENGTH: 1228
<212> TYPE: PRT
<213> ORGANISM: Bacillus thuringiensis

<400

```
              305                 310                 315                 320
Thr Ala Val Ile Arg Ser Pro His Leu Leu Asp Phe Leu Glu Gln Leu
                    325                 330                 335
Thr Ile Phe Ser Thr Ser Ser Arg Trp Ser Ala Thr Arg His Met Thr
                340                 345                 350
Tyr Trp Arg Gly His Thr Ile Gln Ser Arg Pro Ile Gly Gly Gly Leu
            355                 360                 365
Asn Thr Ser Thr His Gly Ser Thr Asn Thr Ser Ile Asn Pro Val Arg
        370                 375                 380
Leu Ser Phe Phe Ser Arg Asp Val Tyr Trp Thr Glu Ser Tyr Ala Gly
385                 390                 395                 400
Val Leu Leu Trp Gly Ile Tyr Leu Glu Pro Ile His Gly Val Pro Thr
                405                 410                 415
Val Arg Phe Asn Phe Arg Asn Pro Gln Asn Thr Phe Glu Arg Gly Thr
                420                 425                 430
Ala Asn Tyr Ser Gln Pro Tyr Glu Ser Pro Gly Leu Gln Leu Lys Asp
            435                 440                 445
Ser Glu Thr Glu Leu Pro Pro Glu Thr Thr Glu Arg Pro Asn Tyr Glu
        450                 455                 460
Ser Tyr Ser His Arg Leu Ser His Ile Gly Leu Ile Ser Gln Ser Arg
465                 470                 475                 480
Val His Val Pro Val Tyr Ser Trp Thr His Arg Ser Ala Asp Arg Thr
                485                 490                 495
Asn Thr Ile Ser Ser Asp Ser Ile Thr Gln Ile Pro Leu Val Lys Ser
                500                 505                 510
Phe Asn Leu Asn Ser Gly Thr Ser Val Val Ser Gly Pro Gly Phe Thr
            515                 520                 525
Gly Gly Asp Ile Ile Arg Thr Asn Val Asn Gly Ser Val Leu Ser Met
        530                 535                 540
Gly Leu Asn Phe Asn Asn Thr Ser Leu Gln Arg Tyr Arg Val Arg Val
545                 550                 555                 560
Arg Tyr Ala Ala Ser Gln Thr Met Val Leu Arg Val Thr Val Gly Gly
                565                 570                 575
Ser Thr Thr Phe Asp Gln Gly Phe Pro Ser Thr Met Ser Ala Asn Glu
                580                 585                 590
Ser Leu Thr Ser Gln Ser Phe Arg Phe Ala Glu Phe Pro Val Gly Ile
            595                 600                 605
Ser Ala Ser Gly Ser Gln Thr Ala Gly Ile Ser Ile Ser Asn Asn Ala
        610                 615                 620
Gly Arg Gln Thr Phe His Phe Asp Lys Ile Glu Phe Ile Pro Ile Thr
625                 630                 635                 640
Ala Thr Phe Glu Ala Glu Tyr Asp Leu Glu Arg Ala Gln Glu Ala Val
                645                 650                 655
Asn Ala Leu Phe Thr Asn Thr Asn Pro Arg Arg Leu Lys Thr Asp Val
                660                 665                 670
Thr Asp Tyr His Ile Asp Gln Val Ser Asn Leu Val Ala Cys Leu Ser
            675                 680                 685
Asp Glu Phe Cys Leu Asp Glu Lys Arg Glu Leu Leu Glu Lys Val Lys
        690                 695                 700
Tyr Ala Lys Arg Leu Ser Asp Glu Arg Asn Leu Leu Gln Asp Pro Asn
705                 710                 715                 720
Phe Thr Ser Ile Asn Lys Gln Pro Asp Phe Ile Ser Thr Asn Glu Gln
                725                 730                 735
```

```
Ser Asn Phe Thr Ser Ile His Glu Gln Ser Glu His Gly Trp Trp Gly
            740                 745                 750

Ser Glu Asn Ile Thr Ile Gln Glu Gly Asn Asp Val Phe Lys Glu Asn
                755                 760                 765

Tyr Val Thr Leu Pro Gly Thr Phe Asn Glu Cys Tyr Pro Thr Tyr Leu
    770                 775                 780

Tyr Gln Lys Ile Gly Glu Ser Glu Leu Lys Ala Tyr Thr Arg Tyr Gln
785                 790                 795                 800

Leu Arg Gly Tyr Ile Glu Asp Ser Gln Asp Leu Glu Ile Tyr Leu Ile
                    805                 810                 815

Arg Tyr Asn Ala Lys His Glu Thr Leu Asp Val Pro Gly Thr Glu Ser
            820                 825                 830

Val Trp Pro Leu Ser Val Glu Ser Pro Ile Gly Arg Cys Gly Glu Pro
        835                 840                 845

Asn Arg Cys Ala Pro His Phe Glu Trp Asn Pro Asp Leu Asp Cys Ser
    850                 855                 860

Cys Arg Asp Gly Glu Lys Cys Ala His His Ser His His Phe Ser Leu
865                 870                 875                 880

Asp Ile Asp Ile Gly Cys Thr Asp Leu His Glu Asn Leu Gly Val Trp
                    885                 890                 895

Val Val Phe Lys Ile Lys Thr Gln Glu Gly His Ala Arg Leu Gly Asn
            900                 905                 910

Leu Glu Phe Ile Glu Glu Lys Pro Leu Leu Gly Glu Ala Leu Ser Arg
        915                 920                 925

Val Lys Arg Ala Glu Lys Lys Trp Arg Asp Lys Arg Glu Lys Leu Gln
    930                 935                 940

Leu Glu Thr Lys Arg Val Tyr Thr Glu Ala Lys Glu Ala Val Asp Ala
945                 950                 955                 960

Leu Phe Val Asp Ser Gln Tyr Asn Arg Leu Gln Ala Asp Thr Asn Ile
                    965                 970                 975

Gly Met Ile His Ala Ala Asp Lys Leu Val His Arg Ile Arg Glu Ala
            980                 985                 990

Tyr Leu Ser Glu Leu Ser Val Ile Pro Gly Val Asn Ala Glu Ile Phe
        995                 1000                1005

Glu Glu Leu Glu Gly Arg Ile Ile Thr Ala Ile Ser Leu Tyr Asp Ala
    1010                1015                1020

Arg Asn Val Val Lys Asn Gly Asp Phe Asn Asn Gly Leu Ala Cys Trp
1025                1030                1035                1040

Asn Val Lys Gly His Val Asp Val Gln Gln Ser His His Arg Ser Val
                    1045                1050                1055

Leu Val Ile Pro Glu Trp Glu Ala Glu Val Ser Gln Ala Val Arg Val
            1060                1065                1070

Cys Pro Gly Arg Gly Tyr Ile Leu Arg Val Thr Ala Tyr Lys Glu Gly
        1075                1080                1085

Tyr Gly Glu Gly Cys Val Thr Ile His Glu Ile Glu Asn Asn Thr Asp
    1090                1095                1100

Glu Leu Lys Phe Lys Asn Cys Glu Glu Glu Val Tyr Pro Thr Asp
1105                1110                1115                1120

Thr Gly Thr Cys Asn Asp Tyr Thr Ala His Gln Gly Thr Ala Val Cys
                    1125                1130                1135

Asn Ser Arg Asn Ala Gly Tyr Glu Asp Ala Tyr Glu Val Asp Thr Thr
            1140                1145                1150

Ala Ser Val Asn Tyr Lys Pro Thr Tyr Glu Glu Glu Thr Tyr Thr Asp
        1155                1160                1165
```

```
Val Arg Arg Asp Asn His Cys Glu Tyr Asp Arg Gly Tyr Val Asn Tyr
    1170                1175                1180

Pro Pro Leu Pro Ala Gly Tyr Met Thr Lys Glu Leu Glu Tyr Phe Pro
1185                1190                1195                1200

Glu Thr Asp Lys Val Trp Ile Glu Ile Gly Thr Glu Gly Lys Phe
                1205                1210                1215

Ile Val Asp Ser Val Glu Leu Leu Leu Met Glu Glu
            1220                1225

<210> SEQ ID NO 3
<211> LENGTH: 3507
<212> TYPE: DNA
<213> ORGANISM: Bacillus thuringiensis
<220> FEATURE:
<221> NAME/KEY: CDS
<222> LOCATION: (1)..(3507)

<400> SEQUENCE: 3 atg gag ata aat aat cag aac caa tgc ata cca tat aat tgc tta agt     48
Met Glu Ile Asn Asn Gln Asn Gln Cys Ile Pro Tyr Asn Cys Leu Ser
  1               5                  10                  15 aag cct gag gaa gta ttt ttg gat ggg gag agg ata tta cct gat atc     96
Lys Pro Glu Glu Val Phe Leu Asp Gly Glu Arg Ile Leu Pro Asp Ile
                 20                  25                  30 gat cca ctc gaa gtt tct ttg tcg ctt ttg caa ttt ctt ttg aat aac    144
Asp Pro Leu Glu Val Ser Leu Ser Leu Leu Gln Phe Leu Leu Asn Asn
             35                  40                  45 ttt gtt ccg ggg ggg ggg ttt att tca gga tta att gac aaa ata tgg    192
Phe Val Pro Gly Gly Gly Phe Ile Ser Gly Leu Ile Asp Lys Ile Trp
         50                  55                  60 ggg gct ttg aga cca tct gaa tgg gaa tta ttt ctt gca cag att gaa    240
Gly Ala Leu Arg Pro Ser Glu Trp Glu Leu Phe Leu Ala Gln Ile Glu
 65                  70                  75                  80 cag ttg att gat cga aga ata gaa gca aca gta aga gca aaa gca atc    288
Gln Leu Ile Asp Arg Arg Ile Glu Ala Thr Val Arg Ala Lys Ala Ile
                 85                  90                  95 gct gaa tta gaa ggt tta ggg aga agt tat caa cta tat gga gag gca    336
Ala Glu Leu Glu Gly Leu Gly Arg Ser Tyr Gln Leu Tyr Gly Glu Ala
                100                 105                 110 ttt aaa gag tgg gaa aaa act cca gat aac aca gcg gct cgg tct aga    384
Phe Lys Glu Trp Glu Lys Thr Pro Asp Asn Thr Ala Ala Arg Ser Arg
            115                 120                 125 gta act gag aga ttt cgt ata att gat gct caa att gaa gca aat atc    432
Val Thr Glu Arg Phe Arg Ile Ile Asp Ala Gln Ile Glu Ala Asn Ile
        130                 135                 140 cct tcg ttt cgg gtt tcc gga ttt gaa gtg cca ctt cta tcg gtt tat    480
Pro Ser Phe Arg Val Ser Gly Phe Glu Val Pro Leu Leu Ser Val Tyr
145                 150                 155                 160 acc caa gca gct aat ttg cat ctc gct cta tta aga gat tct gtt att    528
Thr Gln Ala Ala Asn Leu His Leu Ala Leu Leu Arg Asp Ser Val Ile
                165                 170                 175 ttt gga gag aga tgg gga ttg tcg act aca aat gtc aat gat atc tat    576
Phe Gly Glu Arg Trp Gly Leu Ser Thr Thr Asn Val Asn Asp Ile Tyr
            180                 185                 190 aat aga caa gtt aag aga att cat gaa tat agc gat cat tgt gta gat    624
Asn Arg Gln Val Lys Arg Ile His Glu Tyr Ser Asp His Cys Val Asp
        195                 200                 205 acg tat aaa aca gaa tta gaa cgt cta gag ttt aga tct ata gcg caa    672
Thr Tyr Lys Thr Glu Leu Glu Arg Leu Glu Phe Arg Ser Ile Ala Gln
    210                 215                 220
```

```
tgg aga ata tat aat cag ttt aga agg gaa ttg aca cta acg gta tta      720
Trp Arg Ile Tyr Asn Gln Phe Arg Arg Glu Leu Thr Leu Thr Val Leu
225                 230                 235                 240 gat att gtc gct ctt ttc ccg aac tat gat ggt aga ctg tat ccg att      768
Asp Ile Val Ala Leu Phe Pro Asn Tyr Asp Gly Arg Leu Tyr Pro Ile
                245                 250                 255 cga aca att tct caa ttg aca aga gaa att tat aca tcc cca gta agc      816
Arg Thr Ile Ser Gln Leu Thr Arg Glu Ile Tyr Thr Ser Pro Val Ser
            260                 265                 270 gaa ttt tat tat ggt ccc att tat aat cat aat atg att ggt acc ttt      864
Glu Phe Tyr Tyr Gly Pro Ile Tyr Asn His Asn Met Ile Gly Thr Phe
        275                 280                 285 att gaa cgg cag cta agg cga cca cat ctt atg gac ttc ttt aac tcc      912
Ile Glu Arg Gln Leu Arg Arg Pro His Leu Met Asp Phe Phe Asn Ser
    290                 295                 300 atg acc atg tat aca tca gat aat aga cgg gaa tat tat tgg tca gga      960
Met Thr Met Tyr Thr Ser Asp Asn Arg Arg Glu Tyr Tyr Trp Ser Gly
305                 310                 315                 320 ctt gaa atg acg gct act ctt act tca gga aat caa gtg tca ttc cct     1008
Leu Glu Met Thr Ala Thr Leu Thr Ser Gly Asn Gln Val Ser Phe Pro
                325                 330                 335 tta gcc ggg act aga ggg aat tca gct cca cca gta tct gtt aga aag     1056
Leu Ala Gly Thr Arg Gly Asn Ser Ala Pro Pro Val Ser Val Arg Lys
            340                 345                 350 act ggt gag gga att tat aga ata tta tcg gaa cca ttt tat tca gca     1104
Thr Gly Glu Gly Ile Tyr Arg Ile Leu Ser Glu Pro Phe Tyr Ser Ala
        355                 360                 365 cct ttt cta ggc acc agt gtg cta gga agt cgc ggg gaa gaa ttt gct     1152
Pro Phe Leu Gly Thr Ser Val Leu Gly Ser Arg Gly Glu Glu Phe Ala
    370                 375                 380 ttt gca tct aat act act aca agt ctg cca tct aca ata tat aga aat     1200
Phe Ala Ser Asn Thr Thr Thr Ser Leu Pro Ser Thr Ile Tyr Arg Asn
385                 390                 395                 400 cgt gga aca gta gat tca tta gtc agc ata ccg cca caa gat tat agc     1248
Arg Gly Thr Val Asp Ser Leu Val Ser Ile Pro Pro Gln Asp Tyr Ser
                405                 410                 415 gta cca ccg cac agg ggg tat agt cat tta tta agt cac gtt acg atg     1296
Val Pro Pro His Arg Gly Tyr Ser His Leu Leu Ser His Val Thr Met
            420                 425                 430 cac aat agt tct cct ata ttc cac tgg acg cat cgt agt gcg aca cct     1344
His Asn Ser Ser Pro Ile Phe His Trp Thr His Arg Ser Ala Thr Pro
        435                 440                 445 aga aat ata att tat cca gat agt atc act caa atc cca gta gtt aag     1392
Arg Asn Ile Ile Tyr Pro Asp Ser Ile Thr Gln Ile Pro Val Val Lys
    450                 455                 460 gct tcg cac ctc tct ggt ggt tca gtt ata aaa gga cct gga cat aca     1440
Ala Ser His Leu Ser Gly Gly Ser Val Ile Lys Gly Pro Gly His Thr
465                 470                 475                 480 ggt gga gat tta ata agc cta cct gta aat aac ttt act cat ttc cga     1488
Gly Gly Asp Leu Ile Ser Leu Pro Val Asn Asn Phe Thr His Phe Arg
                485                 490                 495 atc cca ttt cag gca aac act cca caa agg tat cgt att aga att tgt     1536
Ile Pro Phe Gln Ala Asn Thr Pro Gln Arg Tyr Arg Ile Arg Ile Cys
            500                 505                 510 tat gcg gca gac tca gat ggg act ttg gat agt gga gtt ttc tta agt     1584
Tyr Ala Ala Asp Ser Asp Gly Thr Leu Asp Ser Gly Val Phe Leu Ser
        515                 520                 525 gca gca gca ggg gat ggt ttt aat aca act tct tat agg gcc aca atg     1632
Ala Ala Ala Gly Asp Gly Phe Asn Thr Thr Ser Tyr Arg Ala Thr Met
    530                 535                 540
```

```
agc cct gaa ggt tcc tta aca tct cgt gat ttt caa ttt tta gat tta   1680
Ser Pro Glu Gly Ser Leu Thr Ser Arg Asp Phe Gln Phe Leu Asp Leu
545                 550                 555                 560 aac aca tcg ttt acc tcc gat gta gca tct aac tta tgg tta cat ttt   1728
Asn Thr Ser Phe Thr Ser Asp Val Ala Ser Asn Leu Trp Leu His Phe
                565                 570                 575 ata cgt tat ata cga cca ggg aat ttg tat ata gat aga gcg gaa ttt   1776
Ile Arg Tyr Ile Arg Pro Gly Asn Leu Tyr Ile Asp Arg Ala Glu Phe
            580                 585                 590 atc cca gtg gat gca acc ttc gag gca ggt tat aat tta gaa agg gcg   1824
Ile Pro Val Asp Ala Thr Phe Glu Ala Gly Tyr Asn Leu Glu Arg Ala
        595                 600                 605 caa aag gcg gtg aat gcc ctg ttt act tct aca aac caa aaa gga tta   1872
Gln Lys Ala Val Asn Ala Leu Phe Thr Ser Thr Asn Gln Lys Gly Leu
    610                 615                 620 caa aca gat gtg acg gat tat cat att gat caa gta tcc aat cta gtt   1920
Gln Thr Asp Val Thr Asp Tyr His Ile Asp Gln Val Ser Asn Leu Val
625                 630                 635                 640 gat tgt tta tct gat gag ttt tgc tta gat gaa aag cga aaa ttg tcc   1968
Asp Cys Leu Ser Asp Glu Phe Cys Leu Asp Glu Lys Arg Lys Leu Ser
                645                 650                 655 gag aaa gtc aaa cag gcg aag cga ctc agt gat gag cgg aat tta ctt   2016
Glu Lys Val Lys Gln Ala Lys Arg Leu Ser Asp Glu Arg Asn Leu Leu
            660                 665                 670 cag gat tca aat ttc aga ggc atc aat agg gaa caa gac cgt gga tgg   2064
Gln Asp Ser Asn Phe Arg Gly Ile Asn Arg Glu Gln Asp Arg Gly Trp
        675                 680                 685 aga gga agt acg gat att act atc caa gga gga aac gat gtt ttc aaa   2112
Arg Gly Ser Thr Asp Ile Thr Ile Gln Gly Gly Asn Asp Val Phe Lys
    690                 695                 700 gag aat tac gtt aca cta cca ggt acc ttt gat gcg tgt tat cca aca   2160
Glu Asn Tyr Val Thr Leu Pro Gly Thr Phe Asp Ala Cys Tyr Pro Thr
705                 710                 715                 720 tat ttg tat caa aaa gtc gat gaa tca aaa tta aaa gcc tat acc cgt   2208
Tyr Leu Tyr Gln Lys Val Asp Glu Ser Lys Leu Lys Ala Tyr Thr Arg
                725                 730                 735 tat caa tta aga ggc tat atc gaa gat agt caa gat tta gaa gtc tat   2256
Tyr Gln Leu Arg Gly Tyr Ile Glu Asp Ser Gln Asp Leu Glu Val Tyr
            740                 745                 750 ttg atc cgt tat aat gca aaa tat gaa acg tta aat gtg cca ggt atg   2304
Leu Ile Arg Tyr Asn Ala Lys Tyr Glu Thr Leu Asn Val Pro Gly Met
        755                 760                 765 ggt tct tta tgg cca ctt tca gtc gaa agt cca att gga aag tgt gga   2352
Gly Ser Leu Trp Pro Leu Ser Val Glu Ser Pro Ile Gly Lys Cys Gly
    770                 775                 780 gaa ccg aat cga tgt gtg cca caa ctt gaa tgg aat ccc gat ttc gat   2400
Glu Pro Asn Arg Cys Val Pro Gln Leu Glu Trp Asn Pro Asp Phe Asp
785                 790                 795                 800 tgt tcc tgc aga gac gga gaa aaa tgt gcg cat cat tcg cat cat ttc   2448
Cys Ser Cys Arg Asp Gly Glu Lys Cys Ala His His Ser His His Phe
                805                 810                 815 tcc ttg gac att gat gtt gga tgt aca gac ttg aat gag aac cta ggt   2496
Ser Leu Asp Ile Asp Val Gly Cys Thr Asp Leu Asn Glu Asn Leu Gly
            820                 825                 830 ata tgg gtg ata ttc aag att aag aca cag gat ggt cat gca aga cta   2544
Ile Trp Val Ile Phe Lys Ile Lys Thr Gln Asp Gly His Ala Arg Leu
        835                 840                 845 gga aat cta gaa ttt ctc gaa gag aaa ccg tta tta gga gaa gcg tta   2592
Gly Asn Leu Glu Phe Leu Glu Glu Lys Pro Leu Leu Gly Glu Ala Leu
    850                 855                 860
```

```
gcc cgt gtg aag aga gcg gag aaa aaa tgg aga gac aaa cgt gaa ata    2640
Ala Arg Val Lys Arg Ala Glu Lys Lys Trp Arg Asp Lys Arg Glu Ile
865                 870                 875                 880 ttg caa tca gaa act aat att gtt tat aaa gaa gca aaa gaa gct gta    2688
Leu Gln Ser Glu Thr Asn Ile Val Tyr Lys Glu Ala Lys Glu Ala Val
                885                 890                 895 gat ggt tta ttc gta gat tcc caa tat gag aga tta caa tct gat acg    2736
Asp Gly Leu Phe Val Asp Ser Gln Tyr Glu Arg Leu Gln Ser Asp Thr
            900                 905                 910 aat atc gcc atg att cat gcg gca gat aaa cgc gtt cac cga atc cga    2784
Asn Ile Ala Met Ile His Ala Ala Asp Lys Arg Val His Arg Ile Arg
        915                 920                 925 gag gct tat ctg cca gag ctc tcc gtg att cca ggt gtc aat gca gcg    2832
Glu Ala Tyr Leu Pro Glu Leu Ser Val Ile Pro Gly Val Asn Ala Ala
    930                 935                 940 att ttc gaa gaa tta gaa gga cgt att ttc aca gcc tac tct cta tat    2880
Ile Phe Glu Glu Leu Glu Gly Arg Ile Phe Thr Ala Tyr Ser Leu Tyr
945                 950                 955                 960 gat gcg aga aat gtc att aaa aac ggt gat ttc aat aat ggc tta tca    2928
Asp Ala Arg Asn Val Ile Lys Asn Gly Asp Phe Asn Asn Gly Leu Ser
                965                 970                 975 tgc tgg aat gtg aaa ggg cat gta gat ata aaa cag aat ggt cat cgt    2976
Cys Trp Asn Val Lys Gly His Val Asp Ile Lys Gln Asn Gly His Arg
            980                 985                 990 tct gtt ctt gtt atc cca gaa tgg gaa gca caa gtt tca caa gaa gtt    3024
Ser Val Leu Val Ile Pro Glu Trp Glu Ala Gln Val Ser Gln Glu Val
        995                 1000                1005 cgt gta tgt cca ggt cgt ggc tac atc ctt cgt gtt aca gcg aac aaa    3072
Arg Val Cys Pro Gly Arg Gly Tyr Ile Leu Arg Val Thr Ala Asn Lys
    1010                1015                1020 gaa gga tat gga gaa ggc tgc gta acg att cat gag att gag aat cat    3120
Glu Gly Tyr Gly Glu Gly Cys Val Thr Ile His Glu Ile Glu Asn His
1025                1030                1035                1040 act gaa aaa ctg aag ttt aga aac tgc gaa gaa gag gaa gta tat cca    3168
Thr Glu Lys Leu Lys Phe Arg Asn Cys Glu Glu Glu Glu Val Tyr Pro
                1045                1050                1055 aac aat aca gga acg tgt aat gat tat act gca cac caa caa ggt aca    3216
Asn Asn Thr Gly Thr Cys Asn Asp Tyr Thr Ala His Gln Gln Gly Thr
            1060                1065                1070 gca gga tgc gca gat gca tgt aat acc cgt aat gtc gga tat gaa gat    3264
Ala Gly Cys Ala Asp Ala Cys Asn Thr Arg Asn Val Gly Tyr Glu Asp
        1075                1080                1085 gca tat gaa atg aat act aca aca tct gtt aat tac aaa ccg act tac    3312
Ala Tyr Glu Met Asn Thr Thr Thr Ser Val Asn Tyr Lys Pro Thr Tyr
    1090                1095                1100 gag gaa gaa gta tat aca gat gga cga aga gat aat cct tgt gaa atg    3360
Glu Glu Glu Val Tyr Thr Asp Gly Arg Arg Asp Asn Pro Cys Glu Met
1105                1110                1115                1120 gaa aga ggt tac aca cca tta cca gtt ggt tat gta aca aaa gaa tta    3408
Glu Arg Gly Tyr Thr Pro Leu Pro Val Gly Tyr Val Thr Lys Glu Leu
                1125                1130                1135 gaa tac ttc cct gaa aca aat aca gta tgg att gaa att gga gaa acg    3456
Glu Tyr Phe Pro Glu Thr Asn Thr Val Trp Ile Glu Ile Gly Glu Thr
            1140                1145                1150 gaa ggg aag ttt att gta gac agt gtc gaa tta ctc ctt atg gaa gaa    3504
Glu Gly Lys Phe Ile Val Asp Ser Val Glu Leu Leu Leu Met Glu Glu
        1155                1160                1165 tag                                                                3507

<210> SEQ ID NO 4
```

<211> LENGTH: 1168
<212> TYPE: PRT
<213> ORGANISM: Bacillus thuringiensis

<400> SEQUENCE: 4

```
Met Glu Ile Asn Asn Gln Asn Gln Cys Ile Pro Tyr Asn Cys Leu Ser
  1               5                  10                  15

Lys Pro Glu Glu Val Phe Leu Asp Gly Glu Arg Ile Leu Pro Asp Ile
                 20                  25                  30

Asp Pro Leu Glu Val Ser Leu Ser Leu Gln Phe Leu Leu Asn Asn
             35                  40                  45

Phe Val Pro Gly Gly Phe Ile Ser Gly Leu Ile Asp Lys Ile Trp
 50                  55                  60

Gly Ala Leu Arg Pro Ser Glu Trp Glu Leu Phe Leu Ala Gln Ile Glu
 65                  70                  75                  80

Gln Leu Ile Asp Arg Arg Ile Glu Ala Thr Val Arg Ala Lys Ala Ile
                 85                  90                  95

Ala Glu Leu Glu Gly Leu Gly Arg Ser Tyr Gln Leu Tyr Gly Glu Ala
                100                 105                 110

Phe Lys Glu Trp Glu Lys Thr Pro Asp Asn Thr Ala Ala Arg Ser Arg
            115                 120                 125

Val Thr Glu Arg Phe Arg Ile Ile Asp Ala Gln Ile Glu Ala Asn Ile
130                 135                 140

Pro Ser Phe Arg Val Ser Gly Phe Glu Val Pro Leu Leu Ser Val Tyr
145                 150                 155                 160

Thr Gln Ala Ala Asn Leu His Leu Ala Leu Leu Arg Asp Ser Val Ile
                165                 170                 175

Phe Gly Glu Arg Trp Gly Leu Ser Thr Thr Asn Val Asn Asp Ile Tyr
            180                 185                 190

Asn Arg Gln Val Lys Arg Ile His Glu Tyr Ser Asp His Cys Val Asp
            195                 200                 205

Thr Tyr Lys Thr Glu Leu Glu Arg Leu Glu Phe Arg Ser Ile Ala Gln
210                 215                 220

Trp Arg Ile Tyr Asn Gln Phe Arg Arg Glu Leu Thr Leu Thr Val Leu
225                 230                 235                 240

Asp Ile Val Ala Leu Phe Pro Asn Tyr Asp Gly Arg Leu Tyr Pro Ile
                245                 250                 255

Arg Thr Ile Ser Gln Leu Thr Arg Glu Ile Tyr Thr Ser Pro Val Ser
            260                 265                 270

Glu Phe Tyr Tyr Gly Pro Ile Tyr Asn His Asn Met Ile Gly Thr Phe
            275                 280                 285

Ile Glu Arg Gln Leu Arg Arg Pro His Leu Met Asp Phe Phe Asn Ser
290                 295                 300

Met Thr Met Tyr Thr Ser Asp Asn Arg Arg Glu Tyr Tyr Trp Ser Gly
305                 310                 315                 320

Leu Glu Met Thr Ala Thr Leu Thr Ser Gly Asn Gln Val Ser Phe Pro
                325                 330                 335

Leu Ala Gly Thr Arg Gly Asn Ser Ala Pro Pro Val Ser Val Arg Lys
            340                 345                 350

Thr Gly Glu Gly Ile Tyr Arg Ile Leu Ser Glu Pro Phe Tyr Ser Ala
            355                 360                 365

Pro Phe Leu Gly Thr Ser Val Leu Gly Ser Arg Gly Glu Glu Phe Ala
        370                 375                 380

Phe Ala Ser Asn Thr Thr Thr Ser Leu Pro Ser Thr Ile Tyr Arg Asn
385                 390                 395                 400
```

```
Arg Gly Thr Val Asp Ser Leu Val Ser Ile Pro Pro Gln Asp Tyr Ser
                405                 410                 415

Val Pro Pro His Arg Gly Tyr Ser His Leu Leu Ser His Val Thr Met
                420                 425                 430

His Asn Ser Ser Pro Ile Phe His Trp Thr His Arg Ser Ala Thr Pro
                435                 440                 445

Arg Asn Ile Ile Tyr Pro Asp Ser Ile Thr Gln Ile Pro Val Val Lys
                450                 455                 460

Ala Ser His Leu Ser Gly Gly Ser Val Ile Lys Gly Pro Gly His Thr
465                 470                 475                 480

Gly Gly Asp Leu Ile Ser Leu Pro Val Asn Asn Phe Thr His Phe Arg
                485                 490                 495

Ile Pro Phe Gln Ala Asn Thr Pro Gln Arg Tyr Arg Ile Arg Ile Cys
                500                 505                 510

Tyr Ala Ala Asp Ser Asp Gly Thr Leu Asp Ser Gly Val Phe Leu Ser
                515                 520                 525

Ala Ala Ala Gly Asp Gly Phe Asn Thr Thr Ser Tyr Arg Ala Thr Met
530                 535                 540

Ser Pro Glu Gly Ser Leu Thr Ser Arg Asp Phe Gln Phe Leu Asp Leu
545                 550                 555                 560

Asn Thr Ser Phe Thr Ser Asp Val Ala Ser Asn Leu Trp Leu His Phe
                565                 570                 575

Ile Arg Tyr Ile Arg Pro Gly Asn Leu Tyr Ile Asp Arg Ala Glu Phe
                580                 585                 590

Ile Pro Val Asp Ala Thr Phe Glu Ala Gly Tyr Asn Leu Glu Arg Ala
                595                 600                 605

Gln Lys Ala Val Asn Ala Leu Phe Thr Ser Thr Asn Gln Lys Gly Leu
                610                 615                 620

Gln Thr Asp Val Thr Asp Tyr His Ile Asp Gln Val Ser Asn Leu Val
625                 630                 635                 640

Asp Cys Leu Ser Asp Glu Phe Cys Leu Asp Glu Lys Arg Lys Leu Ser
                645                 650                 655

Glu Lys Val Lys Gln Ala Lys Arg Leu Ser Asp Glu Arg Asn Leu Leu
                660                 665                 670

Gln Asp Ser Asn Phe Arg Gly Ile Asn Arg Glu Gln Asp Arg Gly Trp
                675                 680                 685

Arg Gly Ser Thr Asp Ile Thr Ile Gln Gly Gly Asn Asp Val Phe Lys
690                 695                 700

Glu Asn Tyr Val Thr Leu Pro Gly Thr Phe Asp Ala Cys Tyr Pro Thr
705                 710                 715                 720

Tyr Leu Tyr Gln Lys Val Asp Glu Ser Lys Leu Lys Ala Tyr Thr Arg
                725                 730                 735

Tyr Gln Leu Arg Gly Tyr Ile Glu Asp Ser Gln Asp Leu Glu Val Tyr
                740                 745                 750

Leu Ile Arg Tyr Asn Ala Lys Tyr Glu Thr Leu Asn Val Pro Gly Met
                755                 760                 765

Gly Ser Leu Trp Pro Leu Ser Val Glu Ser Pro Ile Gly Lys Cys Gly
                770                 775                 780

Glu Pro Asn Arg Cys Val Pro Gln Leu Glu Trp Asn Pro Asp Phe Asp
785                 790                 795                 800

Cys Ser Cys Arg Asp Gly Glu Lys Cys Ala His His Ser His His Phe
                805                 810                 815

Ser Leu Asp Ile Asp Val Gly Cys Thr Asp Leu Asn Glu Asn Leu Gly
```

```
                    820                 825                 830
Ile Trp Val Ile Phe Lys Ile Lys Thr Gln Asp Gly His Ala Arg Leu
            835                 840                 845
Gly Asn Leu Glu Phe Leu Glu Glu Lys Pro Leu Leu Gly Glu Ala Leu
        850                 855                 860
Ala Arg Val Lys Arg Ala Glu Lys Lys Trp Arg Asp Lys Arg Glu Ile
865                 870                 875                 880
Leu Gln Ser Glu Thr Asn Ile Val Tyr Lys Glu Ala Lys Glu Ala Val
                885                 890                 895
Asp Gly Leu Phe Val Asp Ser Gln Tyr Glu Arg Leu Gln Ser Asp Thr
            900                 905                 910
Asn Ile Ala Met Ile His Ala Ala Asp Lys Arg Val His Arg Ile Arg
        915                 920                 925
Glu Ala Tyr Leu Pro Glu Leu Ser Val Ile Pro Gly Val Asn Ala Ala
        930                 935                 940
Ile Phe Glu Glu Leu Glu Gly Arg Ile Phe Thr Ala Tyr Ser Leu Tyr
945                 950                 955                 960
Asp Ala Arg Asn Val Ile Lys Asn Gly Asp Phe Asn Asn Gly Leu Ser
                965                 970                 975
Cys Trp Asn Val Lys Gly His Val Asp Ile Lys Gln Asn Gly His Arg
            980                 985                 990
Ser Val Leu Val Ile Pro Glu Trp Glu Ala Gln Val Ser Gln Glu Val
                995                1000                1005
Arg Val Cys Pro Gly Arg Gly Tyr Ile Leu Arg Val Thr Ala Asn Lys
        1010                1015                1020
Glu Gly Tyr Gly Glu Gly Cys Val Thr Ile His Glu Ile Glu Asn His
1025                1030                1035                1040
Thr Glu Lys Leu Lys Phe Arg Asn Cys Glu Glu Glu Val Tyr Pro
                1045                1050                1055
Asn Asn Thr Gly Thr Cys Asn Asp Tyr Thr Ala His Gln Gln Gly Thr
            1060                1065                1070
Ala Gly Cys Ala Asp Ala Cys Asn Thr Arg Asn Val Gly Tyr Glu Asp
        1075                1080                1085
Ala Tyr Glu Met Asn Thr Thr Thr Ser Val Asn Tyr Lys Pro Thr Tyr
        1090                1095                1100
Glu Glu Glu Val Tyr Thr Asp Gly Arg Arg Asp Asn Pro Cys Glu Met
1105                1110                1115                1120
Glu Arg Gly Tyr Thr Pro Leu Pro Val Gly Tyr Val Thr Lys Glu Leu
                1125                1130                1135
Glu Tyr Phe Pro Glu Thr Asn Thr Val Trp Ile Glu Ile Gly Glu Thr
            1140                1145                1150
Glu Gly Lys Phe Ile Val Asp Ser Val Glu Leu Leu Leu Met Glu Glu
        1155                1160                1165

<210> SEQ ID NO 5
<211> LENGTH: 3459
<212> TYPE: DNA
<213> ORGANISM: Bacillus thuringiensis
<220> FEATURE:
<221> NAME/KEY: CDS
<222> LOCATION: (1)..(3459)

<400> SEQUENCE: 5 atg aac cga aat aat caa aat gat tat gaa gtt att gac gct tcc aat      48
Met Asn Arg Asn Asn Gln Asn Asp Tyr Glu Val Ile Asp Ala Ser Asn
  1               5                  10                  15
```

-continued

| | | | | | | | | | | | | | | | | |
|---|---|---|---|---|---|---|---|---|---|---|---|---|---|---|---|---|
| tgt | ggt | tgt | gcg | tca | gat | gat | gtt | gtt | caa | tac | cct | ttg | gca | aga | gat | 96 |
| Cys | Gly | Cys | Ala | Ser | Asp | Asp | Val | Val | Gln | Tyr | Pro | Leu | Ala | Arg | Asp | |
| | | | 20 | | | | | 25 | | | | | 30 | | | |
| ccg | aat | gct | gta | ttc | caa | aat | atg | cat | tat | aaa | gat | tat | ttg | caa | acg | 144 |
| Pro | Asn | Ala | Val | Phe | Gln | Asn | Met | His | Tyr | Lys | Asp | Tyr | Leu | Gln | Thr | |
| | | 35 | | | | | 40 | | | | | 45 | | | | |
| tat | gat | gga | gac | tat | aca | ggt | tct | ttt | ata | aat | cct | aac | tta | tct | att | 192 |
| Tyr | Asp | Gly | Asp | Tyr | Thr | Gly | Ser | Phe | Ile | Asn | Pro | Asn | Leu | Ser | Ile | |
| | 50 | | | | | 55 | | | | | 60 | | | | | |
| aat | cct | aga | gat | gta | ctg | caa | act | gga | att | aat | att | gtg | gga | aga | tta | 240 |
| Asn | Pro | Arg | Asp | Val | Leu | Gln | Thr | Gly | Ile | Asn | Ile | Val | Gly | Arg | Leu | |
| 65 | | | | | 70 | | | | | 75 | | | | | 80 | |
| cta | gga | ttt | cta | ggt | gtt | cca | ttt | gct | ggt | cag | tta | gtt | act | ttc | tat | 288 |
| Leu | Gly | Phe | Leu | Gly | Val | Pro | Phe | Ala | Gly | Gln | Leu | Val | Thr | Phe | Tyr | |
| | | | | 85 | | | | | 90 | | | | | 95 | | |
| act | ttt | ctt | tta | aat | caa | cta | tgg | cca | aca | aat | gat | aat | gca | gta | tgg | 336 |
| Thr | Phe | Leu | Leu | Asn | Gln | Leu | Trp | Pro | Thr | Asn | Asp | Asn | Ala | Val | Trp | |
| | | | 100 | | | | | 105 | | | | | 110 | | | |
| gaa | gct | ttt | atg | gca | caa | ata | gaa | gag | ctt | att | aat | caa | aga | ata | tcc | 384 |
| Glu | Ala | Phe | Met | Ala | Gln | Ile | Glu | Glu | Leu | Ile | Asn | Gln | Arg | Ile | Ser | |
| | | 115 | | | | | 120 | | | | | 125 | | | | |
| gaa | gca | gta | gta | ggg | aca | gca | gcg | gat | cat | tta | acg | gga | tta | cac | gat | 432 |
| Glu | Ala | Val | Val | Gly | Thr | Ala | Ala | Asp | His | Leu | Thr | Gly | Leu | His | Asp | |
| | 130 | | | | | 135 | | | | | 140 | | | | | |
| aat | tat | gag | tta | tat | gta | gag | gca | ttg | gaa | gaa | tgg | ctg | gaa | aga | ccg | 480 |
| Asn | Tyr | Glu | Leu | Tyr | Val | Glu | Ala | Leu | Glu | Glu | Trp | Leu | Glu | Arg | Pro | |
| 145 | | | | | 150 | | | | | 155 | | | | | 160 | |
| aat | gct | gct | aga | act | aat | cta | ctt | ttt | aat | aga | ttt | acc | acc | cta | gat | 528 |
| Asn | Ala | Ala | Arg | Thr | Asn | Leu | Leu | Phe | Asn | Arg | Phe | Thr | Thr | Leu | Asp | |
| | | | | 165 | | | | | 170 | | | | | 175 | | |
| agt | ctt | ttt | aca | caa | ttt | atg | cca | agc | ttt | ggt | act | gga | cct | gga | agt | 576 |
| Ser | Leu | Phe | Thr | Gln | Phe | Met | Pro | Ser | Phe | Gly | Thr | Gly | Pro | Gly | Ser | |
| | | | 180 | | | | | 185 | | | | | 190 | | | |
| caa | aac | tac | gca | gtt | cca | tta | ctt | aca | gta | tac | gca | caa | gca | gcg | aac | 624 |
| Gln | Asn | Tyr | Ala | Val | Pro | Leu | Leu | Thr | Val | Tyr | Ala | Gln | Ala | Ala | Asn | |
| | | 195 | | | | | 200 | | | | | 205 | | | | |
| ctt | cat | ttg | tta | tta | tta | aag | gat | gct | gaa | ata | tat | gga | gca | aga | tgg | 672 |
| Leu | His | Leu | Leu | Leu | Leu | Lys | Asp | Ala | Glu | Ile | Tyr | Gly | Ala | Arg | Trp | |
| | 210 | | | | | 215 | | | | | 220 | | | | | |
| gga | ctg | aac | caa | aat | cag | att | aac | tca | ttc | cat | acg | cgc | caa | caa | gag | 720 |
| Gly | Leu | Asn | Gln | Asn | Gln | Ile | Asn | Ser | Phe | His | Thr | Arg | Gln | Gln | Glu | |
| 225 | | | | | 230 | | | | | 235 | | | | | 240 | |
| cgt | act | caa | tat | tat | aca | aat | cat | tgc | gta | acg | acg | tat | aat | acc | ggt | 768 |
| Arg | Thr | Gln | Tyr | Tyr | Thr | Asn | His | Cys | Val | Thr | Thr | Tyr | Asn | Thr | Gly | |
| | | | | 245 | | | | | 250 | | | | | 255 | | |
| tta | gat | aga | tta | aga | ggc | aca | aat | act | gaa | agt | tgg | tta | aat | tat | cat | 816 |
| Leu | Asp | Arg | Leu | Arg | Gly | Thr | Asn | Thr | Glu | Ser | Trp | Leu | Asn | Tyr | His | |
| | | | 260 | | | | | 265 | | | | | 270 | | | |
| cga | ttc | cgt | aga | gag | atg | aca | tta | atg | gca | atg | gat | tta | gtg | gcc | tta | 864 |
| Arg | Phe | Arg | Arg | Glu | Met | Thr | Leu | Met | Ala | Met | Asp | Leu | Val | Ala | Leu | |
| | | 275 | | | | | 280 | | | | | 285 | | | | |
| ttc | cca | tac | tat | aat | gtg | cga | caa | tat | cca | aat | ggg | gca | aat | cca | cag | 912 |
| Phe | Pro | Tyr | Tyr | Asn | Val | Arg | Gln | Tyr | Pro | Asn | Gly | Ala | Asn | Pro | Gln | |
| | 290 | | | | | 295 | | | | | 300 | | | | | |
| ctt | aca | cgt | gaa | ata | tat | acg | gat | cca | atc | gta | tat | aat | cca | cca | gct | 960 |
| Leu | Thr | Arg | Glu | Ile | Tyr | Thr | Asp | Pro | Ile | Val | Tyr | Asn | Pro | Pro | Ala | |
| 305 | | | | | 310 | | | | | 315 | | | | | 320 | |
| aat | cag | gga | atc | tgc | cga | cgt | tgg | ggg | aat | aat | cct | tat | aat | aca | ttt | 1008 |
| Asn | Gln | Gly | Ile | Cys | Arg | Arg | Trp | Gly | Asn | Asn | Pro | Tyr | Asn | Thr | Phe | |
| | | | | 325 | | | | | 330 | | | | | 335 | | |

```
                                                        -continued
tct gaa ctt gaa aat gct ttt att cgc ccg cca cat ctt ttt gat agg   1056
Ser Glu Leu Glu Asn Ala Phe Ile Arg Pro Pro His Leu Phe Asp Arg
        340                 345                 350 ttg aat aga tta act att tct aga aac cga tat aca gct cca aca act   1104
Leu Asn Arg Leu Thr Ile Ser Arg Asn Arg Tyr Thr Ala Pro Thr Thr
            355                 360                 365 aat agc tac cta gac tat tgg tca ggt cat act tta caa agc cag tat   1152
Asn Ser Tyr Leu Asp Tyr Trp Ser Gly His Thr Leu Gln Ser Gln Tyr
        370                 375                 380 gca aat aac ccg acg aca tat gaa act agt tac ggt cag att acc tct   1200
Ala Asn Asn Pro Thr Thr Tyr Glu Thr Ser Tyr Gly Gln Ile Thr Ser
385                 390                 395                 400 aac aca cgt tta ttc aat acg act aat gga gcc aat gca ata gat tca   1248
Asn Thr Arg Leu Phe Asn Thr Thr Asn Gly Ala Asn Ala Ile Asp Ser
            405                 410                 415 agg gca aga aat ttt ggt aac tta tac gct aat ttg tat ggt gtt agc   1296
Arg Ala Arg Asn Phe Gly Asn Leu Tyr Ala Asn Leu Tyr Gly Val Ser
        420                 425                 430 tat ttg aat att ttc cca aca ggt gtg atg agt gaa atc acc tca gcc   1344
Tyr Leu Asn Ile Phe Pro Thr Gly Val Met Ser Glu Ile Thr Ser Ala
            435                 440                 445 cct aat acg tgt tgg caa gac ctt act aca act gag gaa cta cca cta   1392
Pro Asn Thr Cys Trp Gln Asp Leu Thr Thr Thr Glu Glu Leu Pro Leu
        450                 455                 460 gtg aat aat aat ttt aat ctt tta tct cat gtt act ttc tta cgc ttc   1440
Val Asn Asn Asn Phe Asn Leu Leu Ser His Val Thr Phe Leu Arg Phe
465                 470                 475                 480 aat act act cag ggt ggc ccc ctt gca act gta ggg ttt gta ccc aca   1488
Asn Thr Thr Gln Gly Gly Pro Leu Ala Thr Val Gly Phe Val Pro Thr
            485                 490                 495 tat gtg tgg aca cgt caa gat gta gat ttt aat aat ata att act ccc   1536
Tyr Val Trp Thr Arg Gln Asp Val Asp Phe Asn Asn Ile Ile Thr Pro
        500                 505                 510 aat aga att act caa ata cca gtg gta aag gca tat gag cta agt agt   1584
Asn Arg Ile Thr Gln Ile Pro Val Val Lys Ala Tyr Glu Leu Ser Ser
            515                 520                 525 ggt gct act gtc gtg aaa ggt cca gga ttc aca gga gga gat gta atc   1632
Gly Ala Thr Val Val Lys Gly Pro Gly Phe Thr Gly Gly Asp Val Ile
530                 535                 540 cga aga aca aat act ggt gga ttc gga gca ata agg gtg tcg gtc act   1680
Arg Arg Thr Asn Thr Gly Gly Phe Gly Ala Ile Arg Val Ser Val Thr
545                 550                 555                 560 gga ccg cta aca caa cga tat cgc ata agg ttc cgt tat gct tcg aca   1728
Gly Pro Leu Thr Gln Arg Tyr Arg Ile Arg Phe Arg Tyr Ala Ser Thr
            565                 570                 575 ata gat ttt gat ttc ttt gta aca cgt gga gga act act ata aat aat   1776
Ile Asp Phe Asp Phe Phe Val Thr Arg Gly Gly Thr Thr Ile Asn Asn
        580                 585                 590 ttt aga ttt aca cgt aca atg aac agg gga cag gaa tca aga tat gaa   1824
Phe Arg Phe Thr Arg Thr Met Asn Arg Gly Gln Glu Ser Arg Tyr Glu
            595                 600                 605 tcc tat cgt act gta gag ttt aca act cct ttt aac ttt aca caa agt   1872
Ser Tyr Arg Thr Val Glu Phe Thr Thr Pro Phe Asn Phe Thr Gln Ser
        610                 615                 620 caa gat ata att cga aca tct atc cag gga ctt agt gga aat ggg gaa   1920
Gln Asp Ile Ile Arg Thr Ser Ile Gln Gly Leu Ser Gly Asn Gly Glu
625                 630                 635                 640 gta tac ctt gat aga att gaa atc atc cct gta aat cca aca cga gaa   1968
Val Tyr Leu Asp Arg Ile Glu Ile Ile Pro Val Asn Pro Thr Arg Glu
            645                 650                 655
```

```
gcg gaa gag gat tta gaa gcg gcg aag aaa gcg gtg gcg agc ttg ttt    2016
Ala Glu Glu Asp Leu Glu Ala Ala Lys Lys Ala Val Ala Ser Leu Phe
            660                 665                 670 aca cgc aca agg gac gga tta caa gta aat gtg aca gat tat caa gtc    2064
Thr Arg Thr Arg Asp Gly Leu Gln Val Asn Val Thr Asp Tyr Gln Val
        675                 680                 685 gat caa gcg gca aat tta gtg tca tgc tta tca gat gaa caa tat gcg    2112
Asp Gln Ala Ala Asn Leu Val Ser Cys Leu Ser Asp Glu Gln Tyr Ala
    690                 695                 700 cat gat aaa aag atg tta ttg gaa gcg gta cgc gcg gca aaa cgc ctc    2160
His Asp Lys Lys Met Leu Leu Glu Ala Val Arg Ala Ala Lys Arg Leu
705                 710                 715                 720 agc cga gaa cgt aac tta ctt cag gat cca gat ttt aat aca atc aat    2208
Ser Arg Glu Arg Asn Leu Leu Gln Asp Pro Asp Phe Asn Thr Ile Asn
                725                 730                 735 agt aca gaa gaa aat gga tgg aaa gca agt aac ggc gtt act att agt    2256
Ser Thr Glu Glu Asn Gly Trp Lys Ala Ser Asn Gly Val Thr Ile Ser
            740                 745                 750 gag ggc ggt cca ttc tat aaa ggc cgt gca ctt cag cta gca agt gca    2304
Glu Gly Gly Pro Phe Tyr Lys Gly Arg Ala Leu Gln Leu Ala Ser Ala
        755                 760                 765 cga gaa aat tac cca aca tac atc tat caa aaa gta gat gca tcg gag    2352
Arg Glu Asn Tyr Pro Thr Tyr Ile Tyr Gln Lys Val Asp Ala Ser Glu
    770                 775                 780 tta aaa cct tat aca cga tat aga ctg gat ggg ttc gtg aag agt agt    2400
Leu Lys Pro Tyr Thr Arg Tyr Arg Leu Asp Gly Phe Val Lys Ser Ser
785                 790                 795                 800 caa gat tta gaa att gat ctc att cac cat cat aaa gtc cat ctt gtg    2448
Gln Asp Leu Glu Ile Asp Leu Ile His His His Lys Val His Leu Val
                805                 810                 815 aaa aat gta cta gat aat tta gta tct gat act tac cca gat gat tct    2496
Lys Asn Val Leu Asp Asn Leu Val Ser Asp Thr Tyr Pro Asp Asp Ser
            820                 825                 830 tgt agt gga atc aat cga tgt gag gaa caa cag atg gta aat gcg caa    2544
Cys Ser Gly Ile Asn Arg Cys Glu Glu Gln Gln Met Val Asn Ala Gln
        835                 840                 845 ctg gaa aca gaa cat cat cat ccg atg gat tgc tgt gaa gca gct caa    2592
Leu Glu Thr Glu His His His Pro Met Asp Cys Cys Glu Ala Ala Gln
    850                 855                 860 aca cat gag ttt tct tcc tat att gat aca ggg gat tta aat tcg act    2640
Thr His Glu Phe Ser Ser Tyr Ile Asp Thr Gly Asp Leu Asn Ser Thr
865                 870                 875                 880 gta gac cag gga atc tgg gtg atc ttt aaa gtt cga aca aca gat ggt    2688
Val Asp Gln Gly Ile Trp Val Ile Phe Lys Val Arg Thr Thr Asp Gly
                885                 890                 895 tat gcg acg cta gga aat ctt gaa ttg gta gag gtc gga ccg tta ttg    2736
Tyr Ala Thr Leu Gly Asn Leu Glu Leu Val Glu Val Gly Pro Leu Leu
            900                 905                 910 ggt gaa cct cta gaa cgt gaa caa aga gaa aat gcg aaa tgg aat gca    2784
Gly Glu Pro Leu Glu Arg Glu Gln Arg Glu Asn Ala Lys Trp Asn Ala
        915                 920                 925 gag tta gga aga aaa cgt gca gaa aca gat cgc gtg tat caa gat gcc    2832
Glu Leu Gly Arg Lys Arg Ala Glu Thr Asp Arg Val Tyr Gln Asp Ala
    930                 935                 940 aaa caa tcc atc aat cat tta ttt gtg gat tat caa gat caa caa tta    2880
Lys Gln Ser Ile Asn His Leu Phe Val Asp Tyr Gln Asp Gln Gln Leu
945                 950                 955                 960 aat cca caa ata ggg atg gca gat att atg gac gct caa aat ctt gtc    2928
Asn Pro Gln Ile Gly Met Ala Asp Ile Met Asp Ala Gln Asn Leu Val
                965                 970                 975
```

```
gca tca att tca gat gta tat agc gat gca gta ctg caa atc cct gga    2976
Ala Ser Ile Ser Asp Val Tyr Ser Asp Ala Val Leu Gln Ile Pro Gly
            980                 985                 990 att aac tat gag att tac aca gag ctg tcc aat cgc tta caa caa gca    3024
Ile Asn Tyr Glu Ile Tyr Thr Glu Leu Ser Asn Arg Leu Gln Gln Ala
        995                1000                1005 tcg tat ctg tat acg tct cga aat gcg gtg caa aat ggg gac ttt aac    3072
Ser Tyr Leu Tyr Thr Ser Arg Asn Ala Val Gln Asn Gly Asp Phe Asn
   1010                1015                1020 aac ggg cta gat agc tgg aat gca aca gcg ggt gca tcg gta caa cag    3120
Asn Gly Leu Asp Ser Trp Asn Ala Thr Ala Gly Ala Ser Val Gln Gln
1025                1030                1035                1040 gat ggc aat acg cat ttc tta gtt ctt tct cat tgg gat gca caa gtt    3168
Asp Gly Asn Thr His Phe Leu Val Leu Ser His Trp Asp Ala Gln Val
            1045                1050                1055 tcc caa caa ttt aga gtg cag ccg aat tgt aaa tat gta tta cgt gta    3216
Ser Gln Gln Phe Arg Val Gln Pro Asn Cys Lys Tyr Val Leu Arg Val
        1060                1065                1070 aca gca gag aaa gta ggc ggc gga gac gga tac gtg act atc cgg gat    3264
Thr Ala Glu Lys Val Gly Gly Gly Asp Gly Tyr Val Thr Ile Arg Asp
   1075                1080                1085 ggt gct cat cat aca gaa acg ctt aca ttt aat gca tgt gat tat gat    3312
Gly Ala His His Thr Glu Thr Leu Thr Phe Asn Ala Cys Asp Tyr Asp
1090                1095                1100 ata aat ggc acg tac gtg act gat aat acg tat cta aca aaa gaa gtg    3360
Ile Asn Gly Thr Tyr Val Thr Asp Asn Thr Tyr Leu Thr Lys Glu Val
1105                1110                1115                1120 ata ttc tat tca cat aca gaa cac atg tgg gta gag gta aat gaa aca    3408
Ile Phe Tyr Ser His Thr Glu His Met Trp Val Glu Val Asn Glu Thr
            1125                1130                1135 gaa ggt gca ttt cat ata gat agt att gaa ttc gtt gaa aca gaa aag    3456
Glu Gly Ala Phe His Ile Asp Ser Ile Glu Phe Val Glu Thr Glu Lys
        1140                1145                1150 taa                                                                3459

<210> SEQ ID NO 6
<211> LENGTH: 1152
<212> TYPE: PRT
<213> ORGANISM: Bacillus thuringiensis

<400> SEQUENCE: 6

Met Asn Arg Asn Asn Gln Asn Asp Tyr Glu Val Ile Asp Ala Ser Asn
  1               5                  10                  15

Cys Gly Cys Ala Ser Asp Asp Val Val Gln Tyr Pro Leu Ala Arg Asp
             20                  25                  30

Pro Asn Ala Val Phe Gln Asn Met His Tyr Lys Asp Tyr Leu Gln Thr
         35                  40                  45

Tyr Asp Gly Asp Tyr Thr Gly Ser Phe Ile Asn Pro Asn Leu Ser Ile
     50                  55                  60

Asn Pro Arg Asp Val Leu Gln Thr Gly Ile Asn Ile Val Gly Arg Leu
 65                  70                  75                  80

Leu Gly Phe Leu Gly Val Pro Phe Ala Gly Gln Leu Val Thr Phe Tyr
                 85                  90                  95

Thr Phe Leu Leu Asn Gln Leu Trp Pro Thr Asn Asp Asn Ala Val Trp
            100                 105                 110

Glu Ala Phe Met Ala Gln Ile Glu Glu Leu Ile Asn Gln Arg Ile Ser
        115                 120                 125

Glu Ala Val Val Gly Thr Ala Ala Asp His Leu Thr Gly Leu His Asp
    130                 135                 140
```

```
Asn Tyr Glu Leu Tyr Val Glu Ala Leu Glu Glu Trp Leu Glu Arg Pro
145                 150                 155                 160

Asn Ala Ala Arg Thr Asn Leu Leu Phe Asn Arg Phe Thr Thr Leu Asp
            165                 170                 175

Ser Leu Phe Thr Gln Phe Met Pro Ser Phe Gly Thr Gly Pro Gly Ser
        180                 185                 190

Gln Asn Tyr Ala Val Pro Leu Leu Thr Val Tyr Ala Gln Ala Ala Asn
        195                 200                 205

Leu His Leu Leu Leu Leu Lys Asp Ala Glu Ile Tyr Gly Ala Arg Trp
    210                 215                 220

Gly Leu Asn Gln Asn Gln Ile Asn Ser Phe His Thr Arg Gln Gln Glu
225                 230                 235                 240

Arg Thr Gln Tyr Tyr Thr Asn His Cys Val Thr Thr Tyr Asn Thr Gly
            245                 250                 255

Leu Asp Arg Leu Arg Gly Thr Asn Thr Glu Ser Trp Leu Asn Tyr His
        260                 265                 270

Arg Phe Arg Arg Glu Met Thr Leu Met Ala Met Asp Leu Val Ala Leu
    275                 280                 285

Phe Pro Tyr Tyr Asn Val Arg Gln Tyr Pro Asn Gly Ala Asn Pro Gln
290                 295                 300

Leu Thr Arg Glu Ile Tyr Thr Asp Pro Ile Val Tyr Asn Pro Pro Ala
305                 310                 315                 320

Asn Gln Gly Ile Cys Arg Arg Trp Gly Asn Asn Pro Tyr Asn Thr Phe
            325                 330                 335

Ser Glu Leu Glu Asn Ala Phe Ile Arg Pro Pro His Leu Phe Asp Arg
        340                 345                 350

Leu Asn Arg Leu Thr Ile Ser Arg Asn Arg Tyr Thr Ala Pro Thr Thr
    355                 360                 365

Asn Ser Tyr Leu Asp Tyr Trp Ser Gly His Thr Leu Gln Ser Gln Tyr
370                 375                 380

Ala Asn Asn Pro Thr Thr Tyr Glu Thr Ser Tyr Gly Gln Ile Thr Ser
385                 390                 395                 400

Asn Thr Arg Leu Phe Asn Thr Thr Asn Gly Ala Asn Ala Ile Asp Ser
            405                 410                 415

Arg Ala Arg Asn Phe Gly Asn Leu Tyr Ala Asn Leu Tyr Gly Val Ser
        420                 425                 430

Tyr Leu Asn Ile Phe Pro Thr Gly Val Met Ser Glu Ile Thr Ser Ala
    435                 440                 445

Pro Asn Thr Cys Trp Gln Asp Leu Thr Thr Thr Glu Glu Leu Pro Leu
450                 455                 460

Val Asn Asn Asn Phe Asn Leu Leu Ser His Val Thr Phe Leu Arg Phe
465                 470                 475                 480

Asn Thr Thr Gln Gly Gly Pro Leu Ala Thr Val Gly Phe Val Pro Thr
            485                 490                 495

Tyr Val Trp Thr Arg Gln Asp Val Asp Phe Asn Asn Ile Ile Thr Pro
        500                 505                 510

Asn Arg Ile Thr Gln Ile Pro Val Val Lys Ala Tyr Glu Leu Ser Ser
    515                 520                 525

Gly Ala Thr Val Val Lys Gly Pro Gly Phe Thr Gly Gly Asp Val Ile
530                 535                 540

Arg Arg Thr Asn Thr Gly Gly Phe Gly Ala Ile Arg Val Ser Val Thr
545                 550                 555                 560

Gly Pro Leu Thr Gln Arg Tyr Arg Ile Arg Phe Arg Tyr Ala Ser Thr
```

-continued

```
                565                 570                 575
Ile Asp Phe Asp Phe Val Thr Arg Gly Thr Thr Ile Asn Asn
            580                 585                 590
Phe Arg Phe Thr Arg Thr Met Asn Arg Gly Gln Glu Ser Arg Tyr Glu
            595                 600                 605
Ser Tyr Arg Thr Val Glu Phe Thr Thr Pro Phe Asn Phe Thr Gln Ser
            610                 615                 620
Gln Asp Ile Ile Arg Thr Ser Ile Gln Gly Leu Ser Gly Asn Gly Glu
625                 630                 635                 640
Val Tyr Leu Asp Arg Ile Glu Ile Pro Val Asn Pro Thr Arg Glu
                645                 650                 655
Ala Glu Glu Asp Leu Glu Ala Lys Lys Ala Val Ala Ser Leu Phe
                660                 665                 670
Thr Arg Thr Arg Asp Gly Leu Gln Val Asn Val Thr Asp Tyr Gln Val
            675                 680                 685
Asp Gln Ala Ala Asn Leu Val Ser Cys Leu Ser Asp Glu Gln Tyr Ala
            690                 695                 700
His Asp Lys Lys Met Leu Leu Glu Ala Val Arg Ala Ala Lys Arg Leu
705                 710                 715                 720
Ser Arg Glu Arg Asn Leu Leu Gln Asp Pro Asp Phe Asn Thr Ile Asn
                725                 730                 735
Ser Thr Glu Glu Asn Gly Trp Lys Ala Ser Asn Gly Val Thr Ile Ser
            740                 745                 750
Glu Gly Gly Pro Phe Tyr Lys Gly Arg Ala Leu Gln Leu Ala Ser Ala
            755                 760                 765
Arg Glu Asn Tyr Pro Thr Tyr Ile Tyr Gln Lys Val Asp Ala Ser Glu
            770                 775                 780
Leu Lys Pro Tyr Thr Arg Tyr Arg Leu Asp Gly Phe Val Lys Ser Ser
785                 790                 795                 800
Gln Asp Leu Glu Ile Asp Leu Ile His His His Lys Val His Leu Val
                805                 810                 815
Lys Asn Val Leu Asp Asn Leu Val Ser Asp Thr Tyr Pro Asp Asp Ser
                820                 825                 830
Cys Ser Gly Ile Asn Arg Cys Glu Glu Gln Gln Met Val Asn Ala Gln
            835                 840                 845
Leu Glu Thr Glu His His His Pro Met Asp Cys Cys Glu Ala Ala Gln
            850                 855                 860
Thr His Glu Phe Ser Ser Tyr Ile Asp Thr Gly Asp Leu Asn Ser Thr
865                 870                 875                 880
Val Asp Gln Gly Ile Trp Val Ile Phe Lys Val Arg Thr Thr Asp Gly
            885                 890                 895
Tyr Ala Thr Leu Gly Asn Leu Glu Leu Val Glu Val Gly Pro Leu Leu
            900                 905                 910
Gly Glu Pro Leu Glu Arg Glu Gln Arg Glu Asn Ala Lys Trp Asn Ala
            915                 920                 925
Glu Leu Gly Arg Lys Arg Ala Glu Thr Asp Arg Val Tyr Gln Asp Ala
            930                 935                 940
Lys Gln Ser Ile Asn His Leu Phe Val Asp Tyr Gln Asp Gln Leu
945                 950                 955                 960
Asn Pro Gln Ile Gly Met Ala Asp Ile Met Asp Ala Gln Asn Leu Val
                965                 970                 975
Ala Ser Ile Ser Asp Val Tyr Ser Asp Ala Val Leu Gln Ile Pro Gly
            980                 985                 990
```

-continued

```
Ile Asn Tyr Glu Ile Tyr Thr Glu Leu Ser Asn Arg Leu Gln Gln Ala
        995                 1000                1005

Ser Tyr Leu Tyr Thr Ser Arg Asn Ala Val Gln Asn Gly Asp Phe Asn
    1010                1015                1020

Asn Gly Leu Asp Ser Trp Asn Ala Thr Ala Gly Ala Ser Val Gln Gln
1025                1030                1035                1040

Asp Gly Asn Thr His Phe Leu Val Leu Ser His Trp Asp Ala Gln Val
                1045                1050                1055

Ser Gln Gln Phe Arg Val Gln Pro Asn Cys Lys Tyr Val Leu Arg Val
        1060                1065                1070

Thr Ala Glu Lys Val Gly Gly Gly Asp Gly Tyr Val Thr Ile Arg Asp
        1075                1080                1085

Gly Ala His His Thr Glu Thr Leu Thr Phe Asn Ala Cys Asp Tyr Asp
    1090                1095                1100

Ile Asn Gly Thr Tyr Val Thr Asp Asn Thr Tyr Leu Thr Lys Glu Val
1105                1110                1115                1120

Ile Phe Tyr Ser His Thr Glu His Met Trp Val Glu Val Asn Glu Thr
                1125                1130                1135

Glu Gly Ala Phe His Ile Asp Ser Ile Glu Phe Val Glu Thr Glu Lys
        1140                1145                1150
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: primer
      cry1B.fw

<400> SEQUENCE: 7
cagtccaaac gggtataaac                                          20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: primer
      B.R

<400> SEQUENCE: 8
ctgcttcgaa ggttgcagta                                          20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: primer
      B.F

<400> SEQUENCE: 9
cagcgtatta agtcgatgga                                          20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: primer
      JFW

<400> SEQUENCE: 10

```
gcagctaatg ctaccacatc                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: primer
      JRV

<400> SEQUENCE: 11
gtggcggtat gctgactaat                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: primer
      9FW

<400> SEQUENCE: 12
gyttttattc gcccgccaca                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: primer
      9RV

<400> SEQUENCE: 13
cgacagtags acccactact                                              20
```